(12) United States Patent
Giordano et al.

(10) Patent No.: US 12,318,289 B2
(45) Date of Patent: Jun. 3, 2025

(54) DEVICE FOR THE IN-SITU DELIVERY OF HEART VALVE PROSTHESIS

(71) Applicant: Corcym S.r.l., Milan (IT)

(72) Inventors: Giovanni Giordano, Saluggia (IT); Monica Francesca Achiluzzi, Saluggia (IT)

(73) Assignee: CORCYM S.R.L., Saluggia (IT)

( * ) Notice: Subject to any disclaimer, the term of this patent is extended or adjusted under 35 U.S.C. 154(b) by 1228 days.

(21) Appl. No.: 17/057,502

(22) PCT Filed: May 23, 2018

(86) PCT No.: PCT/IB2018/053646
§ 371 (c)(1),
(2) Date: Nov. 20, 2020

(87) PCT Pub. No.: WO2019/224581
PCT Pub. Date: Nov. 28, 2019

(65) Prior Publication Data
US 2021/0307903 A1    Oct. 7, 2021

(51) Int. Cl.
*A61F 2/24* (2006.01)

(52) U.S. Cl.
CPC .................. *A61F 2/2427* (2013.01)

(58) Field of Classification Search
CPC ...... A61F 2/2427; A61F 2/2436; A61F 2/966; A61F 2/9517
See application file for complete search history.

(56) References Cited

U.S. PATENT DOCUMENTS

| 3,143,742 A | 8/1964 | Cromie |
| 3,334,629 A | 8/1967 | Cohn |

(Continued)

FOREIGN PATENT DOCUMENTS

| CN | 101011298 A | 8/2007 |
| CN | 102869319 A | 1/2013 |

(Continued)

OTHER PUBLICATIONS

Andersen H.R., et al., "Transluminal Implantation of Artificial Heart Valves. Description of a New Expandable Aortic Valve and Initial Results with Implantation by Catheter Technique in Closed Chest Pigs," European Heart Journal, May 1992, vol. 13, pp. 704-708.

(Continued)

*Primary Examiner* — Darwin P Erezo
*Assistant Examiner* — Christina C Lauer
(74) *Attorney, Agent, or Firm* — Crowe & Dunlevy LLC

(57) ABSTRACT

Disclosed herein is a deployment instrument including: a shaft (2) having a longitudinal axis (X1); a handle (3) at a first end of the shaft (2); and a carrier portion (4) at a second end of the shaft (2). The carrier portion (4) is configured for holding an expandable heart valve prosthesis in a radially collapsed condition for delivery to the implantation site. The carrier portion (4) includes a hub (5) fixed to the handle (3) via the shaft (2), a first deployment element (6) and a second deployment element (7), each of said first deployment element (6) and second deployment element (7) configured to hold a corresponding portion of an expandable heart valve N prosthesis in a radially collapsed condition. A drive member (8) is provided which is configured to operate the first deployment element (6) and the second deployment element (7) in first and second opposite directions. The instrument is also provided with a mechanism to allow a displacement of the second deployment element in the second direction independently of the drive member (11).

19 Claims, 9 Drawing Sheets

(56) References Cited

U.S. PATENT DOCUMENTS

| | | |
|---|---|---|
| 3,363,442 A | 1/1968 | Kennedy et al. |
| 3,409,013 A | 11/1968 | Henry et al. |
| 3,514,131 A | 5/1970 | Mckinney et al. |
| 3,540,431 A | 11/1970 | Mobin-Uddin et al. |
| 3,546,710 A | 12/1970 | Shumakov et al. |
| 3,574,865 A | 4/1971 | Hamaker |
| 3,587,115 A | 6/1971 | Shiley et al. |
| 3,608,097 A | 9/1971 | Bellhouse et al. |
| 3,628,535 A | 12/1971 | Ostrowsky et al. |
| 3,642,004 A | 2/1972 | Osthagen et al. |
| 3,657,744 A | 4/1972 | Ersek |
| 3,671,979 A | 6/1972 | Moulopoulos |
| 3,744,060 A | 7/1973 | Bellhouse et al. |
| 3,755,823 A | 9/1973 | Hancock |
| 3,795,246 A | 3/1974 | Sturgeon |
| 3,839,741 A | 10/1974 | Haller |
| 3,868,956 A | 3/1975 | Alfidi et al. |
| 3,874,388 A | 4/1975 | King et al. |
| 3,997,923 A | 12/1976 | Possis |
| 4,011,947 A | 3/1977 | Sawyer |
| 4,035,849 A | 7/1977 | Angell et al. |
| 4,056,854 A | 11/1977 | Boretos et al. |
| 4,086,665 A | 5/1978 | Poirier |
| 4,106,129 A | 8/1978 | Carpentier et al. |
| 4,220,151 A | 9/1980 | Whitney |
| 4,222,126 A | 9/1980 | Boretos et al. |
| 4,233,690 A | 11/1980 | Akins |
| 4,265,694 A | 5/1981 | Boretos et al. |
| 4,291,420 A | 9/1981 | Reul |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,425,908 A | 1/1984 | Simon |
| 4,451,936 A | 6/1984 | Carpentier et al. |
| 4,470,157 A | 9/1984 | Love |
| 4,477,930 A | 10/1984 | Totten et al. |
| 4,501,030 A | 2/1985 | Lane |
| 4,506,394 A | 3/1985 | Bedard |
| 4,574,803 A | 3/1986 | Storz |
| 4,580,568 A | 4/1986 | Gianturco |
| 4,592,340 A | 6/1986 | Boyles |
| 4,601,706 A | 7/1986 | Aillon |
| 4,610,688 A | 9/1986 | Silvestrini et al. |
| 4,612,011 A | 9/1986 | Kautzky |
| 4,624,822 A | 11/1986 | Arru et al. |
| 4,647,283 A | 3/1987 | Carpentier et al. |
| 4,648,881 A | 3/1987 | Carpentier et al. |
| 4,655,218 A | 4/1987 | Kulik et al. |
| 4,655,771 A | 4/1987 | Wallsten |
| 4,662,885 A | 5/1987 | DiPisa, Jr. |
| 4,665,906 A | 5/1987 | Jervis |
| 4,681,908 A | 7/1987 | Broderick et al. |
| 4,684,364 A | 8/1987 | Sawyer et al. |
| 4,692,164 A | 9/1987 | Dzemeshkevich et al. |
| 4,710,192 A | 12/1987 | Liotta et al. |
| 4,722,725 A | 2/1988 | Sawyer et al. |
| 4,732,152 A | 3/1988 | Wallsten et al. |
| 4,733,665 A | 3/1988 | Palmaz |
| 4,758,151 A | 7/1988 | Arru et al. |
| 4,777,951 A | 10/1988 | Cribier et al. |
| 4,784,644 A | 11/1988 | Sawyer et al. |
| 4,787,899 A | 11/1988 | Lazarus |
| 4,787,901 A | 11/1988 | Baykut |
| 4,796,629 A | 1/1989 | Grayzel |
| 4,797,901 A | 1/1989 | Goerne et al. |
| 4,819,751 A | 4/1989 | Shimada et al. |
| 4,834,755 A | 5/1989 | Silvestrini et al. |
| 4,856,516 A | 8/1989 | Hillstead |
| 4,872,874 A | 10/1989 | Taheri |
| 4,878,495 A | 11/1989 | Grayzel |
| 4,878,906 A | 11/1989 | Lindemann et al. |
| 4,883,458 A | 11/1989 | Shiber |
| 4,909,252 A | 3/1990 | Goldberger |
| 4,917,102 A | 4/1990 | Miller et al. |
| 4,922,905 A | 5/1990 | Strecker |
| 4,954,126 A | 9/1990 | Wallsten |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,002,559 A | 3/1991 | Tower |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,042,161 A | 8/1991 | Hodge |
| 5,047,041 A | 9/1991 | Samuels |
| 5,057,092 A | 10/1991 | Webster, Jr. |
| 5,059,177 A | 10/1991 | Towne et al. |
| 5,061,273 A | 10/1991 | Yock |
| 5,084,151 A | 1/1992 | Vallana et al. |
| 5,085,635 A | 2/1992 | Cragg |
| 5,089,015 A | 2/1992 | Ross |
| 5,123,919 A | 6/1992 | Sauter et al. |
| 5,133,845 A | 7/1992 | Vallana et al. |
| 5,139,515 A | 8/1992 | Robicsek |
| 5,152,771 A | 10/1992 | Sabbaghian et al. |
| 5,161,547 A | 11/1992 | Tower |
| 5,163,953 A | 11/1992 | Vince |
| 5,163,954 A | 11/1992 | Curcio et al. |
| 5,167,628 A | 12/1992 | Boyles |
| 5,181,911 A | 1/1993 | Shturman |
| 5,201,757 A | 4/1993 | Heyn et al. |
| 5,217,483 A | 6/1993 | Tower |
| 5,232,445 A | 8/1993 | Bonzel |
| 5,272,909 A | 12/1993 | Nguyen et al. |
| 5,287,848 A | 2/1994 | Cubb et al. |
| 5,295,958 A | 3/1994 | Shturman |
| 5,300,086 A | 4/1994 | Gory et al. |
| 5,304,189 A | 4/1994 | Goldberg et al. |
| 5,312,393 A | 5/1994 | Mastel |
| 5,314,468 A | 5/1994 | Ramos Martinez |
| 5,327,774 A | 7/1994 | Nguyen et al. |
| 5,332,402 A | 7/1994 | Teitelbaum |
| 5,350,398 A | 9/1994 | Pavcnik et al. |
| 5,360,014 A | 11/1994 | Sauter et al. |
| 5,370,684 A | 12/1994 | Vallana et al. |
| 5,370,685 A | 12/1994 | Stevens |
| 5,387,247 A | 2/1995 | Vallana et al. |
| 5,389,106 A | 2/1995 | Tower |
| 5,397,351 A | 3/1995 | Pavcnik et al. |
| 5,411,552 A | 5/1995 | Andersen et al. |
| 5,415,633 A | 5/1995 | Lazarus et al. |
| 5,423,886 A | 6/1995 | Arru et al. |
| 5,431,676 A | 7/1995 | Dubrul et al. |
| 5,433,723 A | 7/1995 | Lindenberg et al. |
| 5,443,446 A | 8/1995 | Shturman |
| 5,445,608 A | 8/1995 | Chen et al. |
| 5,445,646 A | 8/1995 | Euteneuer et al. |
| 5,449,384 A | 9/1995 | Johnson |
| 5,480,424 A | 1/1996 | Cox |
| 5,489,294 A | 2/1996 | McVenes et al. |
| 5,489,296 A | 2/1996 | Love et al. |
| 5,489,297 A | 2/1996 | Duran |
| 5,496,346 A | 3/1996 | Horzewski et al. |
| 5,500,014 A | 3/1996 | Quijano et al. |
| 5,505,689 A | 4/1996 | Kramer et al. |
| 5,507,767 A | 4/1996 | Maeda et al. |
| 5,522,884 A | 6/1996 | Wright |
| 5,545,209 A | 8/1996 | Roberts et al. |
| 5,545,211 A | 8/1996 | An et al. |
| 5,545,214 A | 8/1996 | Stevens |
| 5,545,215 A | 8/1996 | Duran |
| 5,554,185 A | 9/1996 | Block et al. |
| 5,556,414 A | 9/1996 | Turi |
| 5,560,487 A | 10/1996 | Starr |
| 5,575,818 A | 11/1996 | Pinchuk |
| 5,580,922 A | 12/1996 | Park et al. |
| 5,591,195 A | 1/1997 | Taheri et al. |
| 5,609,626 A | 3/1997 | Quijano et al. |
| 5,645,559 A | 7/1997 | Hachtman et al. |
| 5,662,712 A | 9/1997 | Pathak et al. |
| 5,665,115 A | 9/1997 | Cragg |

(56) References Cited

U.S. PATENT DOCUMENTS

| | | |
|---|---|---|
| 5,667,523 A | 9/1997 | Bynon et al. |
| 5,669,919 A | 9/1997 | Sanders et al. |
| 5,672,169 A | 9/1997 | Verbeek |
| 5,674,277 A | 10/1997 | Freitag |
| 5,693,066 A | 12/1997 | Rupp et al. |
| 5,693,083 A | 12/1997 | Baker et al. |
| 5,695,498 A | 12/1997 | Tower |
| 5,698,307 A | 12/1997 | Levy |
| 5,702,368 A | 12/1997 | Stevens et al. |
| 5,712,953 A | 1/1998 | Langs |
| 5,713,953 A | 2/1998 | Vallana et al. |
| 5,716,417 A | 2/1998 | Girard et al. |
| 5,746,709 A | 5/1998 | Rom et al. |
| 5,749,890 A | 5/1998 | Shaknovich |
| 5,766,151 A | 6/1998 | Valley et al. |
| 5,772,693 A | 6/1998 | Brownlee |
| 5,776,187 A | 7/1998 | Krueger et al. |
| 5,782,809 A | 7/1998 | Umeno et al. |
| 5,782,811 A | 7/1998 | Samson et al. |
| 5,800,456 A | 9/1998 | Maeda et al. |
| 5,800,508 A | 9/1998 | Goicoechea et al. |
| 5,800,531 A | 9/1998 | Cosgrove et al. |
| 5,807,405 A | 9/1998 | Vanney et al. |
| 5,810,873 A | 9/1998 | Morales |
| 5,814,096 A | 9/1998 | Lam et al. |
| 5,817,126 A | 10/1998 | Imran |
| 5,824,037 A | 10/1998 | Fogarty et al. |
| 5,824,041 A | 10/1998 | Lenker et al. |
| 5,824,043 A | 10/1998 | Cottone, Jr. |
| 5,824,053 A | 10/1998 | Khosravi et al. |
| 5,824,055 A | 10/1998 | Spiridigliozzi et al. |
| 5,824,056 A | 10/1998 | Rosenberg |
| 5,824,061 A | 10/1998 | Quijano et al. |
| 5,824,064 A | 10/1998 | Taheri |
| 5,840,081 A | 11/1998 | Andersen et al. |
| 5,843,158 A | 12/1998 | Lenker et al. |
| 5,843,244 A | 12/1998 | Pelton et al. |
| 5,849,005 A | 12/1998 | Garrison et al. |
| 5,851,232 A | 12/1998 | Lois |
| 5,855,597 A | 1/1999 | Jayaraman |
| 5,855,601 A | 1/1999 | Bessler et al. |
| 5,860,966 A | 1/1999 | Tower |
| 5,860,996 A | 1/1999 | Urban et al. |
| 5,861,028 A | 1/1999 | Angell |
| 5,868,783 A | 2/1999 | Tower |
| 5,871,489 A | 2/1999 | Ovil |
| 5,876,436 A | 3/1999 | Vanney et al. |
| 5,876,448 A | 3/1999 | Thompson et al. |
| 5,885,228 A | 3/1999 | Rosenman et al. |
| 5,888,201 A | 3/1999 | Stinson et al. |
| 5,891,191 A | 4/1999 | Stinson |
| 5,891,195 A | 4/1999 | Klostermeyer et al. |
| 5,906,619 A | 5/1999 | Olson et al. |
| 5,907,893 A | 6/1999 | Zadno-Azizi et al. |
| 5,913,842 A | 6/1999 | Boyd et al. |
| 5,925,063 A | 7/1999 | Khosravi |
| 5,944,738 A | 8/1999 | Amplatz et al. |
| 5,947,993 A | 9/1999 | Morales |
| 5,951,540 A | 9/1999 | Verbeek |
| 5,951,600 A | 9/1999 | Lemelson |
| 5,954,766 A | 9/1999 | Zadno-Azizi et al. |
| 5,957,949 A | 9/1999 | Leonhardt et al. |
| 5,968,068 A | 10/1999 | Dehdashtian et al. |
| 5,972,016 A | 10/1999 | Morales |
| 5,980,570 A | 11/1999 | Simpson |
| 5,984,957 A | 11/1999 | Laptewicz, Jr. et al. |
| 5,997,573 A | 12/1999 | Quijano et al. |
| 6,010,530 A | 1/2000 | Goicoechea |
| 6,010,531 A | 1/2000 | Donlon et al. |
| 6,019,739 A | 2/2000 | Rhee et al. |
| 6,019,756 A | 2/2000 | Mueller et al. |
| 6,019,790 A | 2/2000 | Holmberg et al. |
| 6,022,370 A | 2/2000 | Tower |
| 6,024,737 A | 2/2000 | Morales |
| 6,027,525 A | 2/2000 | Suh et al. |
| 6,029,671 A | 2/2000 | Stevens et al. |
| 6,030,360 A | 2/2000 | Biggs |
| 6,042,589 A | 3/2000 | Marianne |
| 6,042,598 A | 3/2000 | Tsugita et al. |
| 6,042,607 A | 3/2000 | Williamson, IV et al. |
| 6,051,002 A | 4/2000 | Morales |
| 6,051,014 A | 4/2000 | Jang |
| 6,051,104 A | 4/2000 | Oriaran et al. |
| 6,059,809 A | 5/2000 | Amor et al. |
| 6,059,827 A | 5/2000 | Fenton, Jr. |
| 6,063,102 A | 5/2000 | Morales |
| 6,090,099 A | 7/2000 | Samson et al. |
| 6,106,497 A | 8/2000 | Wang |
| 6,110,200 A | 8/2000 | Hinnenkamp |
| 6,110,201 A | 8/2000 | Quijano et al. |
| 6,125,852 A | 10/2000 | Stevens et al. |
| 6,139,572 A | 10/2000 | Campbell et al. |
| 6,146,366 A | 11/2000 | Schachar |
| 6,159,239 A | 12/2000 | Greenhalgh |
| 6,162,208 A | 12/2000 | Hipps |
| 6,162,245 A | 12/2000 | Jayaraman |
| 6,168,614 B1 | 1/2001 | Andersen et al. |
| 6,171,335 B1 | 1/2001 | Wheatley et al. |
| 6,174,307 B1 | 1/2001 | Daniel et al. |
| 6,187,016 B1 | 2/2001 | Hedges et al. |
| 6,197,143 B1 | 3/2001 | Bodnar |
| 6,200,336 B1 | 3/2001 | Pavcnik et al. |
| 6,202,272 B1 | 3/2001 | Jackson |
| 6,203,550 B1 | 3/2001 | Olson |
| 6,210,408 B1 | 4/2001 | Chandrasekaran et al. |
| 6,218,662 B1 | 4/2001 | Tchakarov et al. |
| 6,221,006 B1 | 4/2001 | Dubrul et al. |
| 6,221,091 B1 | 4/2001 | Khosravi |
| 6,241,757 B1 | 6/2001 | An et al. |
| 6,245,102 B1 | 6/2001 | Jayaraman |
| 6,248,116 B1 | 6/2001 | Chevillon et al. |
| 6,251,093 B1 | 6/2001 | Valley et al. |
| 6,258,114 B1 | 7/2001 | Konya et al. |
| 6,258,115 B1 | 7/2001 | Dubrul |
| 6,258,120 B1 | 7/2001 | McKenzie et al. |
| 6,270,526 B1 | 8/2001 | Cox |
| 6,277,110 B1 | 8/2001 | Morales |
| 6,277,555 B1 | 8/2001 | Duran et al. |
| 6,287,339 B1 | 9/2001 | Vazquez et al. |
| 6,299,637 B1 | 10/2001 | Shaolian et al. |
| 6,299,638 B1 | 10/2001 | Sauter |
| 6,302,906 B1 | 10/2001 | Goicoechea et al. |
| 6,309,382 B1 | 10/2001 | Garrison et al. |
| 6,309,383 B1 | 10/2001 | Campbell et al. |
| 6,309,417 B1 | 10/2001 | Spence et al. |
| 6,312,462 B1 | 11/2001 | McDermott et al. |
| 6,312,465 B1 | 11/2001 | Griffin et al. |
| 6,338,735 B1 | 1/2002 | Stevens |
| 6,346,071 B1 | 2/2002 | Mussivand |
| 6,348,063 B1 | 2/2002 | Yassour et al. |
| 6,350,277 B1 | 2/2002 | Kocur |
| 6,350,281 B1 | 2/2002 | Rhee |
| 6,352,547 B1 | 3/2002 | Brown et al. |
| 6,352,554 B2 | 3/2002 | De Paulis |
| 6,352,708 B1 | 3/2002 | Duran et al. |
| 6,368,355 B1 | 4/2002 | Uflacker |
| 6,371,970 B1 | 4/2002 | Khosravi et al. |
| 6,371,983 B1 | 4/2002 | Lane |
| 6,379,383 B1 | 4/2002 | Palmaz et al. |
| 6,380,457 B1 | 4/2002 | Yurek et al. |
| 6,387,117 B1 | 5/2002 | Arnold, Jr. et al. |
| 6,395,017 B1 | 5/2002 | Dwyer et al. |
| 6,398,807 B1 | 6/2002 | Chouinard et al. |
| 6,402,780 B2 | 6/2002 | Williamson, IV et al. |
| 6,409,750 B1 | 6/2002 | Hyodoh et al. |
| 6,416,474 B1 | 7/2002 | Penner et al. |
| 6,424,885 B1 | 7/2002 | Niemeyer et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,366 B1 | 10/2002 | Seguin |
| 6,461,382 B1 | 10/2002 | Cao |
| 6,468,303 B1 | 10/2002 | Amplatz et al. |

(56) References Cited

U.S. PATENT DOCUMENTS

| | | |
|---|---|---|
| 6,475,239 B1 | 11/2002 | Campbell et al. |
| 6,481,262 B2 | 11/2002 | Ching et al. |
| 6,482,228 B1 | 11/2002 | Norred |
| 6,488,704 B1 | 12/2002 | Connelly et al. |
| 6,493,608 B1 | 12/2002 | Niemeyer |
| 6,494,909 B2 | 12/2002 | Greenhalgh |
| 6,503,272 B2 | 1/2003 | Duerig et al. |
| 6,506,201 B2 | 1/2003 | Di Caprio et al. |
| 6,508,833 B2 | 1/2003 | Pavcnik et al. |
| 6,510,722 B1 | 1/2003 | Ching et al. |
| 6,520,987 B1 | 2/2003 | Plante |
| 6,527,800 B1 | 3/2003 | McGuckin, Jr. et al. |
| 6,530,949 B2 | 3/2003 | Konya et al. |
| 6,530,952 B2 | 3/2003 | Vesely |
| 6,544,285 B1 | 4/2003 | Thubrikar et al. |
| 6,562,031 B2 | 5/2003 | Chandrasekaran et al. |
| 6,562,058 B2 | 5/2003 | Seguin et al. |
| 6,569,196 B1 | 5/2003 | Vesely |
| 6,572,642 B2 | 6/2003 | Rinaldi et al. |
| 6,582,462 B1 | 6/2003 | Andersen et al. |
| 6,585,758 B1 | 7/2003 | Chouinard et al. |
| 6,592,546 B1 | 7/2003 | Barbut et al. |
| 6,598,307 B2 | 7/2003 | Love et al. |
| 6,605,112 B1 | 8/2003 | Moll et al. |
| 6,607,553 B1 | 8/2003 | Healy et al. |
| 6,613,077 B2 | 9/2003 | Gilligan et al. |
| 6,622,604 B1 | 9/2003 | Chouinard et al. |
| 6,629,350 B2 | 10/2003 | Motsenbocker |
| 6,629,534 B1 | 10/2003 | St. Goar et al. |
| 6,635,068 B1 | 10/2003 | Dubrul et al. |
| 6,641,558 B1 | 11/2003 | Aboul-Hosn et al. |
| 6,645,197 B2 | 11/2003 | Garrison et al. |
| 6,645,220 B1 | 11/2003 | Huter et al. |
| 6,652,571 B1 | 11/2003 | White et al. |
| 6,652,578 B2 | 11/2003 | Bailey et al. |
| 6,656,213 B2 | 12/2003 | Solem |
| 6,656,219 B1 | 12/2003 | Wiktor |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,676,684 B1 | 1/2004 | Morley et al. |
| 6,676,692 B2 | 1/2004 | Rabkin et al. |
| 6,676,698 B2 | 1/2004 | McGuckin, Jr. et al. |
| 6,678,962 B1 | 1/2004 | Love et al. |
| 6,679,893 B1 | 1/2004 | Tran |
| 6,679,911 B2 | 1/2004 | Burgermeister |
| 6,682,558 B2 | 1/2004 | Tu et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,692,513 B2 | 2/2004 | Streeter et al. |
| 6,695,878 B2 | 2/2004 | McGuckin, Jr. et al. |
| 6,702,851 B1 | 3/2004 | Chinn et al. |
| 6,716,241 B2 | 4/2004 | Wilder et al. |
| 6,719,789 B2 | 4/2004 | Cox |
| 6,726,648 B2 | 4/2004 | Kaplon et al. |
| 6,726,651 B1 | 4/2004 | Robinson et al. |
| 6,726,712 B1 | 4/2004 | Raeder-Devens et al. |
| 6,726,713 B2 | 4/2004 | Schaldach et al. |
| 6,730,118 B2 | 5/2004 | Spenser et al. |
| 6,730,377 B2 | 5/2004 | Wang |
| 6,733,525 B2 | 5/2004 | Yang et al. |
| 6,736,846 B2 | 5/2004 | Cox |
| 6,752,828 B2 | 6/2004 | Thornton |
| 6,758,855 B2 | 7/2004 | Fulton, III et al. |
| 6,767,362 B2 | 7/2004 | Schreck |
| 6,769,161 B2 | 8/2004 | Brown et al. |
| 6,769,434 B2 | 8/2004 | Liddicoat et al. |
| 6,786,925 B1 | 9/2004 | Schoon et al. |
| 6,790,229 B1 | 9/2004 | Berreklouw |
| 6,790,230 B2 | 9/2004 | Beyersdorf et al. |
| 6,792,979 B2 | 9/2004 | Konya et al. |
| 6,797,002 B2 | 9/2004 | Spence et al. |
| 6,805,711 B2 | 10/2004 | Quijano et al. |
| 6,821,297 B2 | 11/2004 | Snyders |
| 6,830,575 B2 | 12/2004 | Stenzel et al. |
| 6,830,584 B1 | 12/2004 | Seguin |
| 6,830,585 B1 | 12/2004 | Artof et al. |
| 6,846,324 B2 | 1/2005 | Stobie |
| 6,846,325 B2 | 1/2005 | Liddicoat |
| 6,866,650 B2 | 3/2005 | Stevens et al. |
| 6,872,223 B2 | 3/2005 | Roberts et al. |
| 6,875,231 B2 | 4/2005 | Anduiza et al. |
| 6,883,522 B2 | 4/2005 | Spence et al. |
| 6,887,266 B2 | 5/2005 | Williams et al. |
| 6,890,330 B2 | 5/2005 | Streeter et al. |
| 6,893,460 B2 | 5/2005 | Spenser et al. |
| 6,896,690 B1 | 5/2005 | Lambrecht et al. |
| 6,908,481 B2 | 6/2005 | Cribier |
| 6,913,600 B2 | 7/2005 | Valley et al. |
| 6,913,618 B2 | 7/2005 | Denardo et al. |
| 6,915,560 B2 | 7/2005 | Austin |
| 6,929,653 B2 | 8/2005 | Strecter |
| 6,936,066 B2 | 8/2005 | Palmaz et al. |
| 6,939,365 B1 | 9/2005 | Fogarty et al. |
| 6,945,957 B2 | 9/2005 | Freyman |
| 6,951,571 B1 | 10/2005 | Srivastava |
| 6,964,673 B2 | 11/2005 | Tsugita et al. |
| 6,966,924 B2 | 11/2005 | Holmberg |
| 6,968,607 B2 | 11/2005 | Motsenbocker |
| 6,974,464 B2 | 12/2005 | Quijano et al. |
| 6,974,474 B2 | 12/2005 | Pavcnik et al. |
| 6,974,476 B2 | 12/2005 | McGuckin, Jr. et al. |
| 6,981,942 B2 | 1/2006 | Khaw et al. |
| 6,981,982 B2 | 1/2006 | Armstrong et al. |
| 6,986,742 B2 | 1/2006 | Hart et al. |
| 6,988,881 B2 | 1/2006 | Motsenbocker et al. |
| 6,989,027 B2 | 1/2006 | Allen et al. |
| 6,989,028 B2 | 1/2006 | Lashinski et al. |
| 6,991,646 B2 | 1/2006 | Clerc et al. |
| 6,991,649 B2 | 1/2006 | Sievers |
| 7,001,423 B2 | 2/2006 | Euteneuer et al. |
| 7,007,396 B2 | 3/2006 | Rudko et al. |
| 7,011,681 B2 | 3/2006 | Vesely |
| 7,018,401 B1 | 3/2006 | Hyodoh et al. |
| 7,018,404 B2 | 3/2006 | Holmberg et al. |
| 7,018,406 B2 | 3/2006 | Seguin et al. |
| 7,018,408 B2 | 3/2006 | Bailey et al. |
| 7,021,114 B2 | 4/2006 | Perreault |
| 7,041,128 B2 | 5/2006 | McGuckin, Jr. et al. |
| 7,041,132 B2 | 5/2006 | Quijano et al. |
| 7,044,966 B2 | 5/2006 | Svanidze et al. |
| 7,048,014 B2 | 5/2006 | Hyodoh et al. |
| 7,069,794 B2 | 7/2006 | Motsenbocker et al. |
| 7,077,801 B2 | 7/2006 | Haverich |
| 7,097,659 B2 | 8/2006 | Woolfson et al. |
| 7,101,396 B2 | 9/2006 | Artof et al. |
| 7,105,016 B2 | 9/2006 | Shiu et al. |
| 7,115,141 B2 | 10/2006 | Menz et al. |
| 7,125,418 B2 | 10/2006 | Duran et al. |
| 7,128,759 B2 | 10/2006 | Osborne et al. |
| 7,144,364 B2 | 12/2006 | Barbut et al. |
| 7,147,663 B1 | 12/2006 | Berg et al. |
| 7,153,324 B2 | 12/2006 | Case et al. |
| 7,156,872 B2 | 1/2007 | Strecker |
| 7,160,319 B2 | 1/2007 | Chouinard et al. |
| 7,175,656 B2 | 2/2007 | Khairkhahan |
| 7,186,265 B2 | 3/2007 | Sharkawy et al. |
| 7,195,641 B2 | 3/2007 | Palmaz et al. |
| 7,198,646 B2 | 4/2007 | Figulla et al. |
| 7,201,761 B2 | 4/2007 | Woolfson et al. |
| 7,201,772 B2 | 4/2007 | Schwammenthal et al. |
| 7,211,107 B2 | 5/2007 | Bruckheime et al. |
| 7,252,682 B2 | 8/2007 | Seguin |
| 7,255,706 B2 | 8/2007 | Rosengart |
| 7,258,698 B2 | 8/2007 | Lemmon |
| 7,261,732 B2 | 8/2007 | Justino |
| 7,276,078 B2 | 10/2007 | Spenser et al. |
| 7,300,457 B2 | 11/2007 | Palmaz |
| 7,300,463 B2 | 11/2007 | Liddicoat |
| 7,316,706 B2 | 1/2008 | Bloom et al. |
| 7,329,278 B2 | 2/2008 | Seguin et al. |

(56) References Cited

U.S. PATENT DOCUMENTS

| | | |
|---|---|---|
| 7,329,279 B2 | 2/2008 | Haug et al. |
| 7,335,218 B2 | 2/2008 | Wilson et al. |
| 7,338,467 B2 | 3/2008 | Lutter |
| 7,338,484 B2 | 3/2008 | Schoon et al. |
| 7,338,520 B2 | 3/2008 | Bailey et al. |
| 7,347,869 B2 | 3/2008 | Hojeibane et al. |
| 7,351,256 B2 | 4/2008 | Hojeibane et al. |
| 7,357,814 B2 | 4/2008 | Gabbay |
| 7,367,984 B2 | 5/2008 | Kulcinski et al. |
| 7,374,571 B2 | 5/2008 | Pease et al. |
| 7,377,938 B2 | 5/2008 | Sarac et al. |
| 7,377,941 B2 | 5/2008 | Rhee et al. |
| RE40,377 E | 6/2008 | Williamson, IV et al. |
| 7,381,218 B2 | 6/2008 | Schreck |
| 7,381,220 B2 | 6/2008 | Macoviak et al. |
| 7,384,411 B1 | 6/2008 | Condado |
| 7,393,360 B2 | 7/2008 | Spenser et al. |
| 7,399,315 B2 | 7/2008 | Iobbi |
| 7,427,291 B2 | 9/2008 | Liddicoat et al. |
| 7,429,269 B2 | 9/2008 | Schwammenthal et al. |
| 7,442,204 B2 | 10/2008 | Schwammenthal et al. |
| 7,453,227 B2 | 11/2008 | Prisco et al. |
| 7,455,690 B2 | 11/2008 | Cartledge et al. |
| 7,462,191 B2 | 12/2008 | Spenser et al. |
| 7,470,284 B2 | 12/2008 | Lambrecht et al. |
| 7,481,838 B2 | 1/2009 | Carpentier et al. |
| 7,534,259 B2 | 5/2009 | Lashinski et al. |
| 7,544,206 B2 | 6/2009 | Cohn |
| 7,547,322 B2 | 6/2009 | Sarac et al. |
| 7,556,645 B2 | 7/2009 | Lashinski et al. |
| 7,556,646 B2 | 7/2009 | Yang et al. |
| 7,569,071 B2 | 8/2009 | Haverkost et al. |
| 7,578,843 B2 | 8/2009 | Shu |
| 7,585,321 B2 | 9/2009 | Cribier |
| 7,591,843 B1 | 9/2009 | Escano et al. |
| 7,591,848 B2 | 9/2009 | Allen |
| 7,618,432 B2 | 11/2009 | Pedersen et al. |
| 7,618,446 B2 | 11/2009 | Andersen et al. |
| 7,618,447 B2 | 11/2009 | Case et al. |
| 7,635,386 B1 | 12/2009 | Gammie |
| 7,648,528 B2 | 1/2010 | Styrc |
| 7,682,390 B2 | 3/2010 | Seguin |
| 7,708,775 B2 | 5/2010 | Rowe et al. |
| 7,717,955 B2 | 5/2010 | Lane et al. |
| 7,753,949 B2 | 7/2010 | Lamphere et al. |
| 7,758,640 B2 | 7/2010 | Vesely |
| 7,776,083 B2 | 8/2010 | Vesely |
| 7,780,726 B2 | 8/2010 | Seguin |
| 7,785,341 B2 | 8/2010 | Forster et al. |
| 7,806,919 B2 | 10/2010 | Bloom et al. |
| 7,806,927 B2 | 10/2010 | Styrc |
| 7,857,845 B2 | 12/2010 | Stacchino et al. |
| 7,892,281 B2 | 2/2011 | Seguin et al. |
| 7,896,915 B2 | 3/2011 | Guyenot et al. |
| 7,959,672 B2 | 6/2011 | Salahieh et al. |
| 7,972,378 B2 | 7/2011 | Tabor et al. |
| 7,981,153 B2 | 7/2011 | Fogarty et al. |
| 7,993,392 B2 | 8/2011 | Righini et al. |
| 8,006,535 B2 | 8/2011 | Righini et al. |
| 8,016,882 B2 | 9/2011 | Macoviak et al. |
| 8,025,695 B2 | 9/2011 | Fogarty et al. |
| 8,034,103 B2 | 10/2011 | Burriesci et al. |
| 8,043,360 B2 | 10/2011 | McNamara et al. |
| 8,048,153 B2 | 11/2011 | Salahieh et al. |
| 8,057,539 B2 | 11/2011 | Ghione et al. |
| 8,070,799 B2 | 12/2011 | Righini et al. |
| 8,070,802 B2 | 12/2011 | Lamphere et al. |
| 8,080,053 B2 | 12/2011 | Satasiya et al. |
| 8,083,793 B2 | 12/2011 | Lane et al. |
| 8,105,375 B2 | 1/2012 | Navia et al. |
| 8,109,996 B2 | 2/2012 | Stacchino et al. |
| 8,114,154 B2 | 2/2012 | Righini et al. |
| 8,167,935 B2 | 5/2012 | McGuckin, Jr. et al. |
| 8,211,169 B2 | 7/2012 | Lane et al. |
| 8,221,493 B2 | 7/2012 | Boyle et al. |
| 8,236,049 B2 | 8/2012 | Rowe et al. |
| 8,287,591 B2 | 10/2012 | Keidar et al. |
| 8,298,244 B2 | 10/2012 | Garcia et al. |
| 8,323,335 B2 | 12/2012 | Rowe et al. |
| 8,398,708 B2 | 3/2013 | Meiri et al. |
| 8,403,983 B2 | 3/2013 | Quadri et al. |
| 8,414,644 B2 | 4/2013 | Quadri et al. |
| 8,449,599 B2 | 5/2013 | Chau et al. |
| 8,454,686 B2 | 6/2013 | Alkhatib |
| 8,470,024 B2 | 6/2013 | Ghione et al. |
| 8,475,521 B2 | 7/2013 | Suri et al. |
| 8,486,137 B2 | 7/2013 | Suri et al. |
| 8,535,373 B2 | 9/2013 | Stacchino et al. |
| 8,539,662 B2 | 9/2013 | Stacchino et al. |
| 8,540,767 B2 | 9/2013 | Zhang |
| 8,540,768 B2 | 9/2013 | Stacchino et al. |
| 8,579,964 B2 | 11/2013 | Lane et al. |
| 8,579,966 B2 | 11/2013 | Seguin et al. |
| 8,597,348 B2 | 12/2013 | Rowe et al. |
| 8,753,393 B2 | 6/2014 | Strasly et al. |
| 8,808,369 B2 | 8/2014 | Suri |
| 8,822,219 B2 | 9/2014 | Strasly et al. |
| 8,834,563 B2 | 9/2014 | Righini |
| 8,840,661 B2 | 9/2014 | Manasse |
| 8,920,492 B2 | 12/2014 | Stacchino et al. |
| 9,161,836 B2 | 10/2015 | Rolando et al. |
| 9,186,249 B2 | 11/2015 | Rolando et al. |
| 9,248,017 B2 | 2/2016 | Rolando et al. |
| 9,289,289 B2 | 3/2016 | Rolando et al. |
| 9,415,567 B2 | 8/2016 | Sogard et al. |
| 9,486,313 B2 | 11/2016 | Stacchino et al. |
| 9,848,981 B2 | 12/2017 | Suri et al. |
| 9,867,695 B2 | 1/2018 | Stacchino et al. |
| 9,895,223 B2 | 2/2018 | Stacchino et al. |
| 10,098,733 B2 | 10/2018 | Righini |
| 10,201,418 B2 | 2/2019 | Biadillah et al. |
| 10,709,555 B2 | 7/2020 | Schreck et al. |
| 10,799,555 B2 | 10/2020 | Gutierrez et al. |
| 10,973,629 B2 | 4/2021 | Levi et al. |
| 11,185,405 B2 | 11/2021 | Girard et al. |
| 11,197,754 B2 | 12/2021 | Saffari et al. |
| 11,357,624 B2 | 6/2022 | Guyenot et al. |
| 2001/0001314 A1 | 5/2001 | Davison et al. |
| 2001/0002445 A1 | 5/2001 | Vesely |
| 2001/0007956 A1 | 7/2001 | Letac et al. |
| 2001/0010017 A1 | 7/2001 | Letac et al. |
| 2001/0011189 A1 | 8/2001 | Drasler et al. |
| 2001/0021872 A1 | 9/2001 | Bailey et al. |
| 2001/0025196 A1 | 9/2001 | Chinn et al. |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2001/0044591 A1 | 11/2001 | Stevens et al. |
| 2001/0044647 A1 | 11/2001 | Pinchuk et al. |
| 2001/0049558 A1 | 12/2001 | Liddicoat et al. |
| 2002/0010508 A1 | 1/2002 | Chobotov |
| 2002/0029014 A1 | 3/2002 | Jayaraman |
| 2002/0029075 A1 | 3/2002 | Leonhardt |
| 2002/0029783 A1 | 3/2002 | Stevens et al. |
| 2002/0032480 A1 | 3/2002 | Spence et al. |
| 2002/0032481 A1 | 3/2002 | Gabbay |
| 2002/0035390 A1 | 3/2002 | Schaldach et al. |
| 2002/0035396 A1 | 3/2002 | Heath |
| 2002/0042650 A1 | 4/2002 | Vardi et al. |
| 2002/0042651 A1 | 4/2002 | Liddicoat et al. |
| 2002/0045846 A1 | 4/2002 | Kaplon et al. |
| 2002/0045929 A1 | 4/2002 | Diaz |
| 2002/0058994 A1 | 5/2002 | Hill et al. |
| 2002/0058995 A1 | 5/2002 | Stevens |
| 2002/0072789 A1 | 6/2002 | Hackett et al. |
| 2002/0095209 A1 | 7/2002 | Zadno-Azizi et al. |
| 2002/0099431 A1 | 7/2002 | Armstrong et al. |
| 2002/0103533 A1 | 8/2002 | Langberg et al. |
| 2002/0107531 A1 | 8/2002 | Schreck et al. |
| 2002/0107565 A1 | 8/2002 | Greenhalgh |
| 2002/0111674 A1 | 8/2002 | Chouinard et al. |
| 2002/0117264 A1 | 8/2002 | Rinaldi et al. |
| 2002/0123802 A1 | 9/2002 | Snyders |
| 2002/0128702 A1 | 9/2002 | Menz et al. |

(56) References Cited

U.S. PATENT DOCUMENTS

| | | |
|---|---|---|
| 2002/0129820 A1 | 9/2002 | Ryan et al. |
| 2002/0133183 A1 | 9/2002 | Lentz et al. |
| 2002/0133226 A1 | 9/2002 | Marquez et al. |
| 2002/0138138 A1 | 9/2002 | Yang |
| 2002/0151970 A1 | 10/2002 | Garrison et al. |
| 2002/0161377 A1 | 10/2002 | Rabkin |
| 2002/0161392 A1 | 10/2002 | Dubrul |
| 2002/0161394 A1 | 10/2002 | Macoviak et al. |
| 2002/0183839 A1 | 12/2002 | Garrison et al. |
| 2002/0193871 A1 | 12/2002 | Beyersdorf et al. |
| 2002/0198594 A1 | 12/2002 | Schreck |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0028247 A1 | 2/2003 | Cali |
| 2003/0033000 A1 | 2/2003 | DiCaprio et al. |
| 2003/0036791 A1 | 2/2003 | Philipp et al. |
| 2003/0036795 A1 | 2/2003 | Andersen et al. |
| 2003/0040771 A1 | 2/2003 | Hyodoh et al. |
| 2003/0040772 A1 | 2/2003 | Hyodoh et al. |
| 2003/0050694 A1 | 3/2003 | Yang et al. |
| 2003/0055495 A1 | 3/2003 | Pease et al. |
| 2003/0065386 A1 | 4/2003 | Weadock |
| 2003/0069492 A1 | 4/2003 | Abrams et al. |
| 2003/0109924 A1 | 6/2003 | Cribier |
| 2003/0114913 A1 | 6/2003 | Spenser et al. |
| 2003/0125795 A1 | 7/2003 | Pavcnik et al. |
| 2003/0125805 A1 | 7/2003 | Johnson et al. |
| 2003/0130726 A1 | 7/2003 | Thorpe et al. |
| 2003/0130729 A1 | 7/2003 | Paniagua et al. |
| 2003/0139804 A1 | 7/2003 | Hankh et al. |
| 2003/0149475 A1 | 8/2003 | Hyodoh et al. |
| 2003/0149476 A1 | 8/2003 | Damm et al. |
| 2003/0149478 A1 | 8/2003 | Figulla et al. |
| 2003/0153974 A1 | 8/2003 | Spenser et al. |
| 2003/0163194 A1 | 8/2003 | Quijano et al. |
| 2003/0181850 A1 | 9/2003 | Diamond et al. |
| 2003/0191519 A1 | 10/2003 | Lombardi et al. |
| 2003/0191521 A1 | 10/2003 | Denardo et al. |
| 2003/0191528 A1 | 10/2003 | Quijano et al. |
| 2003/0192164 A1 | 10/2003 | Austin |
| 2003/0199913 A1 | 10/2003 | Dubrul et al. |
| 2003/0199963 A1 | 10/2003 | Tower et al. |
| 2003/0208261 A1 | 11/2003 | Thorpe et al. |
| 2003/0212410 A1 | 11/2003 | Stenzel et al. |
| 2003/0212454 A1 | 11/2003 | Scott et al. |
| 2003/0225445 A1 | 12/2003 | Derus et al. |
| 2004/0019374 A1 | 1/2004 | Hojeibane et al. |
| 2004/0034407 A1 | 2/2004 | Sherry |
| 2004/0034411 A1 | 2/2004 | Quijano et al. |
| 2004/0039371 A1 | 2/2004 | Tockman et al. |
| 2004/0039436 A1 | 2/2004 | Spenser et al. |
| 2004/0039442 A1 | 2/2004 | St. Goar et al. |
| 2004/0049224 A1 | 3/2004 | Buehlmann et al. |
| 2004/0049262 A1 | 3/2004 | Obermiller et al. |
| 2004/0049266 A1 | 3/2004 | Anduiza et al. |
| 2004/0055606 A1 | 3/2004 | Hendricksen et al. |
| 2004/0073301 A1 | 4/2004 | Donlon et al. |
| 2004/0078072 A1 | 4/2004 | Tu et al. |
| 2004/0078074 A1 | 4/2004 | Anderson et al. |
| 2004/0082904 A1 | 4/2004 | Houde et al. |
| 2004/0088045 A1 | 5/2004 | Cox |
| 2004/0092858 A1 | 5/2004 | Wilson et al. |
| 2004/0092989 A1 | 5/2004 | Wilson et al. |
| 2004/0093005 A1 | 5/2004 | Durcan |
| 2004/0093060 A1 | 5/2004 | Seguin et al. |
| 2004/0093063 A1 | 5/2004 | Wright et al. |
| 2004/0093070 A1 | 5/2004 | Hojeibane et al. |
| 2004/0093075 A1 | 5/2004 | Kuehne |
| 2004/0097788 A1 | 5/2004 | Mourlas et al. |
| 2004/0098112 A1 | 5/2004 | DiMatteo et al. |
| 2004/0106976 A1 | 6/2004 | Bailey et al. |
| 2004/0106990 A1 | 6/2004 | Spence et al. |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0122468 A1 | 6/2004 | Yodfat et al. |
| 2004/0122514 A1 | 6/2004 | Fogarty et al. |
| 2004/0122516 A1 | 6/2004 | Fogarty et al. |
| 2004/0123437 A1 | 7/2004 | Kokish |
| 2004/0127848 A1 | 7/2004 | Freyman |
| 2004/0127979 A1 | 7/2004 | Wilson et al. |
| 2004/0138742 A1 | 7/2004 | Myers et al. |
| 2004/0138743 A1 | 7/2004 | Myers et al. |
| 2004/0147993 A1 | 7/2004 | Westlund et al. |
| 2004/0153146 A1 | 8/2004 | Lashinski et al. |
| 2004/0167573 A1 | 8/2004 | Williamson, IV et al. |
| 2004/0167620 A1 | 8/2004 | Ortiz et al. |
| 2004/0186558 A1 | 9/2004 | Pavcnik et al. |
| 2004/0186563 A1 | 9/2004 | Lobbi |
| 2004/0193259 A1 | 9/2004 | Gabbay |
| 2004/0193261 A1 | 9/2004 | Berreklouw |
| 2004/0210240 A1 | 10/2004 | Saint |
| 2004/0210304 A1 | 10/2004 | Seguin et al. |
| 2004/0210307 A1 | 10/2004 | Khairkhahan |
| 2004/0215333 A1 | 10/2004 | Duran et al. |
| 2004/0215339 A1 | 10/2004 | Drasler et al. |
| 2004/0225353 A1 | 11/2004 | McGuckin, Jr. et al. |
| 2004/0225354 A1 | 11/2004 | Allen et al. |
| 2004/0225355 A1 | 11/2004 | Stevens |
| 2004/0225356 A1 | 11/2004 | Frater |
| 2004/0236170 A1 | 11/2004 | Kim |
| 2004/0249413 A1 | 12/2004 | Allen et al. |
| 2004/0254636 A1 | 12/2004 | Flagle et al. |
| 2004/0260389 A1 | 12/2004 | Case et al. |
| 2004/0260394 A1 | 12/2004 | Douk et al. |
| 2004/0267357 A1 | 12/2004 | Allen et al. |
| 2005/0010246 A1 | 1/2005 | Streeter et al. |
| 2005/0010285 A1 | 1/2005 | Lambrecht et al. |
| 2005/0010287 A1 | 1/2005 | Macoviak et al. |
| 2005/0015112 A1 | 1/2005 | Cohn et al. |
| 2005/0027348 A1 | 2/2005 | Case et al. |
| 2005/0033398 A1 | 2/2005 | Seguin |
| 2005/0043790 A1 | 2/2005 | Seguin |
| 2005/0049692 A1 | 3/2005 | Numamoto et al. |
| 2005/0049696 A1 | 3/2005 | Siess et al. |
| 2005/0055088 A1 | 3/2005 | Liddicoat et al. |
| 2005/0060029 A1 | 3/2005 | Le et al. |
| 2005/0060030 A1 | 3/2005 | Lashinski et al. |
| 2005/0075584 A1 | 4/2005 | Cali |
| 2005/0075712 A1 | 4/2005 | Biancucci et al. |
| 2005/0075713 A1 | 4/2005 | Biancucci et al. |
| 2005/0075717 A1 | 4/2005 | Nguyen et al. |
| 2005/0075718 A1 | 4/2005 | Nguyen et al. |
| 2005/0075719 A1 | 4/2005 | Bergheim |
| 2005/0075720 A1 | 4/2005 | Nguyen et al. |
| 2005/0075724 A1 | 4/2005 | Svanidze et al. |
| 2005/0075726 A1 | 4/2005 | Svanidze et al. |
| 2005/0075727 A1 | 4/2005 | Wheatley |
| 2005/0075728 A1 | 4/2005 | Nguyen et al. |
| 2005/0075729 A1 | 4/2005 | Nguyen et al. |
| 2005/0075730 A1 | 4/2005 | Myers et al. |
| 2005/0075731 A1 | 4/2005 | Artof et al. |
| 2005/0080476 A1 | 4/2005 | Gunderson et al. |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0085900 A1 | 4/2005 | Case et al. |
| 2005/0096568 A1 | 5/2005 | Kato |
| 2005/0096692 A1 | 5/2005 | Linder et al. |
| 2005/0096724 A1 | 5/2005 | Stenzel et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096993 A1 | 5/2005 | Pradhan et al. |
| 2005/0104957 A1 | 5/2005 | Okamoto et al. |
| 2005/0107871 A1 | 5/2005 | Realyvasquez et al. |
| 2005/0113910 A1 | 5/2005 | Paniagua et al. |
| 2005/0119688 A1 | 6/2005 | Bergheim |
| 2005/0131438 A1 | 6/2005 | Cohn |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |

(56) References Cited

U.S. PATENT DOCUMENTS

| | | |
|---|---|---|
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137693 A1 | 6/2005 | Haug et al. |
| 2005/0137694 A1 | 6/2005 | Haug et al. |
| 2005/0137695 A1 | 6/2005 | Salahieh et al. |
| 2005/0137696 A1 | 6/2005 | Salahieh et al. |
| 2005/0137697 A1 | 6/2005 | Salahieh et al. |
| 2005/0137698 A1 | 6/2005 | Salahieh et al. |
| 2005/0137699 A1 | 6/2005 | Salahieh et al. |
| 2005/0137701 A1 | 6/2005 | Salahieh et al. |
| 2005/0137702 A1 | 6/2005 | Haug et al. |
| 2005/0143807 A1 | 6/2005 | Pavcnik et al. |
| 2005/0143809 A1 | 6/2005 | Salahieh et al. |
| 2005/0148997 A1 | 7/2005 | Valley et al. |
| 2005/0149181 A1 | 7/2005 | Eberhardt |
| 2005/0165477 A1 | 7/2005 | Anduiza et al. |
| 2005/0165480 A1 | 7/2005 | Jordan et al. |
| 2005/0166389 A1 | 8/2005 | Perreault et al. |
| 2005/0182486 A1 | 8/2005 | Gabbay |
| 2005/0187616 A1 | 8/2005 | Realyvasquez |
| 2005/0197695 A1 | 9/2005 | Stacchino et al. |
| 2005/0197696 A1 | 9/2005 | Gomez Duran |
| 2005/0203549 A1 | 9/2005 | Realyvasquez |
| 2005/0203605 A1 | 9/2005 | Dolan |
| 2005/0203618 A1 | 9/2005 | Sharkawy et al. |
| 2005/0222674 A1 | 10/2005 | Paine |
| 2005/0222675 A1 | 10/2005 | Sauter |
| 2005/0228495 A1 | 10/2005 | Macoviak |
| 2005/0229670 A1 | 10/2005 | Perreault |
| 2005/0234537 A1 | 10/2005 | Edin |
| 2005/0234546 A1 | 10/2005 | Nugent et al. |
| 2005/0240200 A1 | 10/2005 | Bergheim |
| 2005/0240256 A1 | 10/2005 | Austin |
| 2005/0240263 A1 | 10/2005 | Fogarty et al. |
| 2005/0251251 A1 | 11/2005 | Cribier |
| 2005/0261759 A1 | 11/2005 | Lambrecht et al. |
| 2005/0267493 A1 | 12/2005 | Schreck et al. |
| 2005/0267529 A1 | 12/2005 | Crockett et al. |
| 2005/0278010 A1 | 12/2005 | Richardson |
| 2005/0283232 A1 | 12/2005 | Gabbay |
| 2005/0283962 A1 | 12/2005 | Boudjemline |
| 2006/0004436 A1 | 1/2006 | Amarant et al. |
| 2006/0004439 A1 | 1/2006 | Spenser et al. |
| 2006/0004442 A1 | 1/2006 | Spenser et al. |
| 2006/0004469 A1 | 1/2006 | Sokel |
| 2006/0009841 A1 | 1/2006 | McGuckin, Jr. et al. |
| 2006/0020333 A1 | 1/2006 | Lashinski et al. |
| 2006/0020334 A1 | 1/2006 | Lashinski et al. |
| 2006/0025844 A1 | 2/2006 | Majercak et al. |
| 2006/0025855 A1 | 2/2006 | Lashinski et al. |
| 2006/0029659 A1 | 2/2006 | Panzardi |
| 2006/0030922 A1 | 2/2006 | Dolan |
| 2006/0052867 A1 | 3/2006 | Revuelta et al. |
| 2006/0058775 A1 | 3/2006 | Stevens et al. |
| 2006/0058872 A1 | 3/2006 | Salahieh et al. |
| 2006/0063199 A1 | 3/2006 | Elgebaly et al. |
| 2006/0064054 A1 | 3/2006 | Sakakine et al. |
| 2006/0073592 A1 | 4/2006 | Sun et al. |
| 2006/0074271 A1 | 4/2006 | Cotter |
| 2006/0074484 A1 | 4/2006 | Huber |
| 2006/0074486 A1 | 4/2006 | Liddicoat et al. |
| 2006/0085060 A1 | 4/2006 | Campbell |
| 2006/0089711 A1 | 4/2006 | Dolan |
| 2006/0095025 A1 | 5/2006 | Levine et al. |
| 2006/0095117 A1 | 5/2006 | Popelar et al. |
| 2006/0100639 A1 | 5/2006 | Levin et al. |
| 2006/0100685 A1 | 5/2006 | Seguin et al. |
| 2006/0116757 A1 | 6/2006 | Lashinski et al. |
| 2006/0135962 A1 | 6/2006 | Kick et al. |
| 2006/0135964 A1 | 6/2006 | Vesely |
| 2006/0142838 A1 | 6/2006 | Molaei et al. |
| 2006/0142848 A1 | 6/2006 | Gabbay |
| 2006/0167474 A1 | 7/2006 | Bloom et al. |
| 2006/0178740 A1 | 8/2006 | Stacchino et al. |
| 2006/0190017 A1 | 8/2006 | Cyr et al. |
| 2006/0195134 A1 | 8/2006 | Crittenden |
| 2006/0195183 A1 | 8/2006 | Navia et al. |
| 2006/0195184 A1 | 8/2006 | Lane et al. |
| 2006/0206192 A1 | 9/2006 | Tower et al. |
| 2006/0206202 A1 | 9/2006 | Bonhoeffer et al. |
| 2006/0212111 A1 | 9/2006 | Case et al. |
| 2006/0229659 A1 | 10/2006 | Gifford et al. |
| 2006/0241656 A1 | 10/2006 | Starksen et al. |
| 2006/0247763 A1 | 11/2006 | Slater |
| 2006/0253134 A1 | 11/2006 | Ortiz et al. |
| 2006/0259134 A1 | 11/2006 | Schwammenthal et al. |
| 2006/0259136 A1 | 11/2006 | Nguyen et al. |
| 2006/0259137 A1 | 11/2006 | Artof et al. |
| 2006/0265056 A1 | 11/2006 | Nguyen et al. |
| 2006/0265855 A1 | 11/2006 | Stenzel |
| 2006/0271081 A1 | 11/2006 | Realyvasquez |
| 2006/0271166 A1 | 11/2006 | Thill et al. |
| 2006/0271175 A1 | 11/2006 | Woolfson et al. |
| 2006/0276775 A1 | 12/2006 | Rosenberg et al. |
| 2006/0276874 A1 | 12/2006 | Wilson et al. |
| 2006/0276882 A1 | 12/2006 | Case et al. |
| 2006/0282161 A1 | 12/2006 | Huynh et al. |
| 2007/0005129 A1 | 1/2007 | Damm et al. |
| 2007/0005131 A1 | 1/2007 | Taylor |
| 2007/0010850 A1 | 1/2007 | Balgobin et al. |
| 2007/0010878 A1 | 1/2007 | Rafiee et al. |
| 2007/0016286 A1 | 1/2007 | Herrmann et al. |
| 2007/0027518 A1 | 2/2007 | Case et al. |
| 2007/0027533 A1 | 2/2007 | Douk |
| 2007/0027534 A1 | 2/2007 | Bergheim et al. |
| 2007/0032850 A1 | 2/2007 | Ruiz et al. |
| 2007/0038295 A1 | 2/2007 | Case et al. |
| 2007/0043431 A1 | 2/2007 | Melsheimer |
| 2007/0043435 A1 | 2/2007 | Seguin et al. |
| 2007/0051377 A1 | 3/2007 | Douk et al. |
| 2007/0055357 A1 | 3/2007 | Pokorney et al. |
| 2007/0056346 A1 | 3/2007 | Spenser et al. |
| 2007/0061009 A1 | 3/2007 | Spenser et al. |
| 2007/0073387 A1 | 3/2007 | Forster et al. |
| 2007/0073392 A1 | 3/2007 | Heyninck-Jantz et al. |
| 2007/0078509 A1 | 4/2007 | Lotfy |
| 2007/0078510 A1 | 4/2007 | Ryan |
| 2007/0088431 A1 | 4/2007 | Bourang et al. |
| 2007/0093869 A1 | 4/2007 | Bloom et al. |
| 2007/0093887 A1 | 4/2007 | Case et al. |
| 2007/0093890 A1 | 4/2007 | Eliasen et al. |
| 2007/0100302 A1 | 5/2007 | Dicarlo et al. |
| 2007/0100356 A1 | 5/2007 | Lucatero et al. |
| 2007/0100432 A1 | 5/2007 | Case et al. |
| 2007/0100435 A1 | 5/2007 | Case et al. |
| 2007/0100439 A1 | 5/2007 | Cangialosi et al. |
| 2007/0100440 A1 | 5/2007 | Figulla et al. |
| 2007/0100449 A1 | 5/2007 | O'Neil et al. |
| 2007/0106372 A1 | 5/2007 | Osborne et al. |
| 2007/0112355 A1 | 5/2007 | Salahieh et al. |
| 2007/0112415 A1 | 5/2007 | Bartlett |
| 2007/0112422 A1 | 5/2007 | Dehdashtian |
| 2007/0118207 A1 | 5/2007 | Amplatz et al. |
| 2007/0118209 A1 | 5/2007 | Strecker |
| 2007/0118215 A1 | 5/2007 | Moaddeb |
| 2007/0142968 A1 | 6/2007 | Prisco et al. |
| 2007/0156225 A1 | 7/2007 | George et al. |
| 2007/0162100 A1 | 7/2007 | Gabbay |
| 2007/0162102 A1 | 7/2007 | Ryan et al. |
| 2007/0162103 A1 | 7/2007 | Case et al. |
| 2007/0162107 A1 | 7/2007 | Haug et al. |
| 2007/0162111 A1 | 7/2007 | Fukamachi et al. |
| 2007/0162113 A1 | 7/2007 | Sharkawy et al. |
| 2007/0168024 A1 | 7/2007 | Khairkhahan |
| 2007/0173861 A1 | 7/2007 | Strommer et al. |
| 2007/0185513 A1 | 8/2007 | Woolfson et al. |
| 2007/0203391 A1 | 8/2007 | Bloom et al. |
| 2007/0203503 A1 | 8/2007 | Salahieh et al. |
| 2007/0203561 A1 | 8/2007 | Forster et al. |
| 2007/0203575 A1 | 8/2007 | Forster et al. |
| 2007/0213838 A1 | 9/2007 | Hengelmolen |
| 2007/0219630 A1 | 9/2007 | Chu |

(56) References Cited

U.S. PATENT DOCUMENTS

| | | |
|---|---|---|
| 2007/0225681 A1 | 9/2007 | House |
| 2007/0232898 A1 | 10/2007 | Huynh et al. |
| 2007/0233228 A1 | 10/2007 | Eberhardt et al. |
| 2007/0233237 A1 | 10/2007 | Krivoruchko |
| 2007/0233238 A1 | 10/2007 | Huynh et al. |
| 2007/0237802 A1 | 10/2007 | McKay |
| 2007/0238979 A1 | 10/2007 | Huynh et al. |
| 2007/0239254 A1 | 10/2007 | Chia et al. |
| 2007/0239265 A1 | 10/2007 | Birdsall |
| 2007/0239266 A1 | 10/2007 | Birdsall |
| 2007/0239269 A1 | 10/2007 | Dolan et al. |
| 2007/0239271 A1 | 10/2007 | Nguyen |
| 2007/0239273 A1 | 10/2007 | Allen |
| 2007/0244544 A1 | 10/2007 | Birdsall et al. |
| 2007/0244545 A1 | 10/2007 | Birdsall et al. |
| 2007/0244546 A1 | 10/2007 | Francis |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0244557 A1 | 10/2007 | Rafiee et al. |
| 2007/0250097 A1 | 10/2007 | Weitzner et al. |
| 2007/0250160 A1 | 10/2007 | Rafiee |
| 2007/0255394 A1 | 11/2007 | Ryan |
| 2007/0255396 A1 | 11/2007 | Douk et al. |
| 2007/0260305 A1 | 11/2007 | Drews et al. |
| 2007/0265701 A1 | 11/2007 | Gurskis et al. |
| 2007/0265702 A1 | 11/2007 | Lattouf |
| 2007/0270944 A1 | 11/2007 | Bergheim et al. |
| 2007/0288000 A1 | 12/2007 | Bonan |
| 2007/0288089 A1 | 12/2007 | Gurskis et al. |
| 2007/0293942 A1 | 12/2007 | Mirzaee |
| 2008/0004696 A1 | 1/2008 | Vesely |
| 2008/0009940 A1 | 1/2008 | Cribier |
| 2008/0015671 A1 | 1/2008 | Bonhoeffer |
| 2008/0021546 A1 | 1/2008 | Patz et al. |
| 2008/0021552 A1 | 1/2008 | Gabbay |
| 2008/0048656 A1 | 2/2008 | Tan et al. |
| 2008/0065001 A1 | 3/2008 | DiNucci et al. |
| 2008/0065011 A1 | 3/2008 | Marchand et al. |
| 2008/0065204 A1 | 3/2008 | Macoviak et al. |
| 2008/0065206 A1 | 3/2008 | Liddicoat |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0077234 A1 | 3/2008 | Styrc |
| 2008/0082164 A1 | 4/2008 | Friedman |
| 2008/0082165 A1 | 4/2008 | Wilson et al. |
| 2008/0082166 A1 | 4/2008 | Styrc et al. |
| 2008/0097595 A1 | 4/2008 | Gabbay |
| 2008/0102439 A1 | 5/2008 | Tian et al. |
| 2008/0103586 A1 | 5/2008 | Styrc et al. |
| 2008/0125859 A1 | 5/2008 | Salahieh et al. |
| 2008/0133033 A1 | 6/2008 | Wolff et al. |
| 2008/0140189 A1 | 6/2008 | Nguyen et al. |
| 2008/0147105 A1 | 6/2008 | Wilson et al. |
| 2008/0147160 A1 | 6/2008 | Ghione et al. |
| 2008/0147180 A1 | 6/2008 | Ghione et al. |
| 2008/0147181 A1 | 6/2008 | Ghione et al. |
| 2008/0147182 A1 | 6/2008 | Righini et al. |
| 2008/0147188 A1 | 6/2008 | Steinberg |
| 2008/0154355 A1 | 6/2008 | Benichou et al. |
| 2008/0154356 A1 | 6/2008 | Obermiller et al. |
| 2008/0161910 A1 | 7/2008 | Revuelta et al. |
| 2008/0161911 A1 | 7/2008 | Revuelta et al. |
| 2008/0183097 A1 | 7/2008 | Leyde et al. |
| 2008/0183273 A1 | 7/2008 | Mesana et al. |
| 2008/0188880 A1 | 8/2008 | Fischer et al. |
| 2008/0188928 A1 | 8/2008 | Salahieh et al. |
| 2008/0208216 A1 | 8/2008 | Cerier |
| 2008/0208327 A1 | 8/2008 | Rowe |
| 2008/0215143 A1 | 9/2008 | Seguin |
| 2008/0215144 A1 | 9/2008 | Ryan et al. |
| 2008/0228254 A1 | 9/2008 | Ryan |
| 2008/0228263 A1 | 9/2008 | Ryan |
| 2008/0234797 A1 | 9/2008 | Styrc |
| 2008/0243246 A1 | 10/2008 | Ryan et al. |
| 2008/0249619 A1 | 10/2008 | Stacchino et al. |
| 2008/0255651 A1 | 10/2008 | Dwork |
| 2008/0255660 A1 | 10/2008 | Guyenot et al. |
| 2008/0255661 A1 | 10/2008 | Straubinger et al. |
| 2008/0255662 A1 | 10/2008 | Stacchino et al. |
| 2008/0262507 A1 | 10/2008 | Righini et al. |
| 2008/0262593 A1 | 10/2008 | Ryan et al. |
| 2008/0262603 A1 | 10/2008 | Giaquinta et al. |
| 2008/0269878 A1 | 10/2008 | Iobbi |
| 2009/0005863 A1 | 1/2009 | Goetz et al. |
| 2009/0012600 A1 | 1/2009 | Styrc et al. |
| 2009/0018570 A1 | 1/2009 | Righini et al. |
| 2009/0048656 A1 | 2/2009 | Wen |
| 2009/0054976 A1 | 2/2009 | Tuval et al. |
| 2009/0069886 A1 | 3/2009 | Suri et al. |
| 2009/0069887 A1 | 3/2009 | Righini et al. |
| 2009/0069889 A1 | 3/2009 | Suri et al. |
| 2009/0069890 A1 | 3/2009 | Suri et al. |
| 2009/0082858 A1 | 3/2009 | Nugent et al. |
| 2009/0085900 A1 | 4/2009 | Weiner |
| 2009/0099653 A1 | 4/2009 | Suri et al. |
| 2009/0105794 A1 | 4/2009 | Ziarno et al. |
| 2009/0118580 A1 | 5/2009 | Sun et al. |
| 2009/0125098 A1 | 5/2009 | Chuter |
| 2009/0138079 A1 | 5/2009 | Tuval et al. |
| 2009/0157174 A1 | 6/2009 | Yoganathan et al. |
| 2009/0157175 A1 | 6/2009 | Benichou |
| 2009/0164004 A1 | 6/2009 | Cohn |
| 2009/0164006 A1 | 6/2009 | Seguin et al. |
| 2009/0171363 A1 | 7/2009 | Chocron |
| 2009/0171447 A1 | 7/2009 | Von Segesser et al. |
| 2009/0171456 A1 | 7/2009 | Kveen et al. |
| 2009/0177275 A1 | 7/2009 | Case |
| 2009/0192585 A1 | 7/2009 | Bloom et al. |
| 2009/0192586 A1 | 7/2009 | Tabor et al. |
| 2009/0192591 A1 | 7/2009 | Ryan et al. |
| 2009/0192602 A1 | 7/2009 | Kuehn |
| 2009/0192603 A1 | 7/2009 | Ryan |
| 2009/0198316 A1 | 8/2009 | Laske et al. |
| 2009/0209955 A1 | 8/2009 | Forster et al. |
| 2009/0210025 A1 | 8/2009 | Ameri |
| 2009/0210052 A1 | 8/2009 | Forster et al. |
| 2009/0216310 A1 | 8/2009 | Straubinger et al. |
| 2009/0216312 A1 | 8/2009 | Straubinger et al. |
| 2009/0216313 A1 | 8/2009 | Straubinger et al. |
| 2009/0222082 A1 | 9/2009 | Lock et al. |
| 2009/0222084 A1 | 9/2009 | Friedman |
| 2009/0228093 A1 | 9/2009 | Taylor et al. |
| 2009/0234443 A1 | 9/2009 | Ottma et al. |
| 2009/0240264 A1 | 9/2009 | Tuval et al. |
| 2009/0240320 A1 | 9/2009 | Tuval et al. |
| 2009/0240326 A1 | 9/2009 | Wilson et al. |
| 2009/0248149 A1 | 10/2009 | Gabbay |
| 2009/0254165 A1 | 10/2009 | Tabor et al. |
| 2009/0276040 A1 | 11/2009 | Rowe et al. |
| 2009/0281609 A1 | 11/2009 | Benichou et al. |
| 2009/0281619 A1 | 11/2009 | Le et al. |
| 2009/0287296 A1 | 11/2009 | Manasse |
| 2009/0287299 A1 | 11/2009 | Tabor et al. |
| 2010/0004739 A1 | 1/2010 | Vesely |
| 2010/0004740 A1 | 1/2010 | Seguin et al. |
| 2010/0030328 A1 | 2/2010 | Seguin et al. |
| 2010/0030340 A1 | 2/2010 | Wolfinbarger, Jr. et al. |
| 2010/0036479 A1 | 2/2010 | Hill et al. |
| 2010/0036485 A1 | 2/2010 | Seguin |
| 2010/0049303 A1 | 2/2010 | Guyenot et al. |
| 2010/0049313 A1 | 2/2010 | Alon et al. |
| 2010/0069852 A1 | 3/2010 | Kelley |
| 2010/0094411 A1 | 4/2010 | Tuval et al. |
| 2010/0100167 A1 | 4/2010 | Bortlein et al. |
| 2010/0121434 A1 | 5/2010 | Paul et al. |
| 2010/0131054 A1 | 5/2010 | Tuval et al. |
| 2010/0137979 A1 | 6/2010 | Tuval et al. |
| 2010/0145439 A1 | 6/2010 | Seguin et al. |

(56) References Cited

U.S. PATENT DOCUMENTS

| | | |
|---|---|---|
| 2010/0145440 A1 | 6/2010 | Keranen |
| 2010/0152840 A1 | 6/2010 | Seguin et al. |
| 2010/0161045 A1 | 6/2010 | Righini |
| 2010/0174363 A1 | 7/2010 | Castro |
| 2010/0191326 A1 | 7/2010 | Alkhatib |
| 2010/0198346 A1 | 8/2010 | Keogh et al. |
| 2010/0204781 A1 | 8/2010 | Alkhatib |
| 2010/0234940 A1 | 9/2010 | Dolan |
| 2010/0249661 A1 | 9/2010 | Righini et al. |
| 2010/0256723 A1 | 10/2010 | Murray |
| 2010/0256741 A1 | 10/2010 | Hansen |
| 2010/0262043 A1 | 10/2010 | Sauter et al. |
| 2010/0274351 A1 | 10/2010 | Rolando et al. |
| 2010/0292782 A1 | 11/2010 | Giannetti et al. |
| 2010/0292783 A1 | 11/2010 | Giannetti et al. |
| 2010/0292784 A1 | 11/2010 | Giannetti et al. |
| 2010/0312333 A1 | 12/2010 | Navia et al. |
| 2011/0029072 A1 | 2/2011 | Gabbay |
| 2011/0071624 A1 | 3/2011 | Finch et al. |
| 2011/0082539 A1 | 4/2011 | Suri |
| 2011/0098800 A1 | 4/2011 | Braido et al. |
| 2011/0137397 A1 | 6/2011 | Chau et al. |
| 2011/0166636 A1 | 7/2011 | Rowe |
| 2011/0178597 A9 | 7/2011 | Navia et al. |
| 2011/0218620 A1 | 9/2011 | Meiri et al. |
| 2011/0224785 A1 | 9/2011 | Hacohen |
| 2011/0288636 A1 | 11/2011 | Rolando et al. |
| 2011/0313515 A1 | 12/2011 | Quadri et al. |
| 2012/0010697 A1 | 1/2012 | Shin et al. |
| 2012/0016464 A1 | 1/2012 | Seguin |
| 2012/0022640 A1 | 1/2012 | Gross et al. |
| 2012/0046742 A1 | 2/2012 | Tuval et al. |
| 2012/0053681 A1 | 3/2012 | Alkhatib et al. |
| 2012/0053684 A1 | 3/2012 | Righini |
| 2012/0078353 A1 | 3/2012 | Quadri et al. |
| 2012/0078360 A1 | 3/2012 | Rafiee |
| 2012/0101571 A1 | 4/2012 | Thambar et al. |
| 2012/0165930 A1 | 6/2012 | Gifford, III et al. |
| 2012/0172982 A1 | 7/2012 | Stacchino et al. |
| 2012/0271398 A1 | 10/2012 | Essinger et al. |
| 2012/0303116 A1 | 11/2012 | Gorman, III et al. |
| 2013/0018449 A1 | 1/2013 | Bailey et al. |
| 2013/0035759 A1 | 2/2013 | Gross et al. |
| 2013/0053950 A1 | 2/2013 | Rowe et al. |
| 2013/0123915 A1 | 5/2013 | Giannetti et al. |
| 2013/0144381 A1 | 6/2013 | Quadri et al. |
| 2013/0172991 A1 | 7/2013 | Rolando et al. |
| 2013/0211508 A1 | 8/2013 | Lane et al. |
| 2013/0231735 A1* | 9/2013 | Deem .................. A61F 2/2436 623/2.11 |
| 2013/0231736 A1 | 9/2013 | Essinger et al. |
| 2013/0245753 A1 | 9/2013 | Alkhatib |
| 2013/0325112 A1 | 12/2013 | Stacchino et al. |
| 2013/0345800 A1 | 12/2013 | Stacchino et al. |
| 2014/0046434 A1 | 2/2014 | Rolando et al. |
| 2014/0052243 A1 | 2/2014 | Rolando et al. |
| 2014/0052244 A1 | 2/2014 | Rolando et al. |
| 2014/0088698 A1 | 3/2014 | Roels et al. |
| 2014/0135909 A1* | 5/2014 | Carr .................. A61F 2/2436 623/2.11 |
| 2014/0155997 A1 | 6/2014 | Braido |
| 2014/0350666 A1 | 11/2014 | Righini |
| 2015/0018938 A1 | 1/2015 | Von Segesser et al. |
| 2015/0134052 A1 | 5/2015 | Hariton et al. |
| 2015/0148895 A1 | 5/2015 | Stacchino et al. |
| 2016/0331525 A1 | 11/2016 | Straubinger et al. |
| 2016/0354205 A1 | 12/2016 | Essinger et al. |
| 2017/0035565 A1 | 2/2017 | Stacchino et al. |
| 2017/0056171 A1* | 3/2017 | Cooper ................ A61F 2/2436 |
| 2019/0224005 A1 | 7/2019 | McDonald |

FOREIGN PATENT DOCUMENTS

| | | |
|---|---|---|
| DE | 3640745 A1 | 6/1987 |
| DE | 19532846 A1 | 3/1997 |
| DE | 19546692 A1 | 6/1997 |
| DE | 29911694 U1 | 8/1999 |
| DE | 29919625 U1 | 1/2000 |
| DE | 19857887 A1 | 7/2000 |
| DE | 19907646 A1 | 8/2000 |
| DE | 10010074 A1 | 10/2001 |
| DE | 10049812 A1 | 4/2002 |
| DE | 10049813 C1 | 4/2002 |
| DE | 10049815 A1 | 4/2002 |
| DE | 10121210 A1 | 11/2002 |
| DE | 19546692 C2 | 11/2002 |
| DE | 10301026 A1 | 2/2004 |
| DE | 19857887 B4 | 5/2005 |
| DE | 102004019254 B8 | 11/2005 |
| DE | 202011000848 U1 | 6/2011 |
| EP | 0095970 A2 | 12/1983 |
| EP | 0502410 A1 | 9/1992 |
| EP | 0637454 A1 | 2/1995 |
| EP | 0592410 B1 | 10/1995 |
| EP | 0512359 B1 | 12/1996 |
| EP | 0850607 A1 | 7/1998 |
| EP | 0941716 A2 | 9/1999 |
| EP | 1049425 A1 | 11/2000 |
| EP | 1057460 A1 | 12/2000 |
| EP | 1059271 A1 | 12/2000 |
| EP | 1176913 A2 | 2/2002 |
| EP | 1214050 A1 | 6/2002 |
| EP | 0778009 B1 | 7/2002 |
| EP | 1251803 A1 | 10/2002 |
| EP | 1255510 A1 | 11/2002 |
| EP | 1335683 A2 | 8/2003 |
| EP | 1343438 A2 | 9/2003 |
| EP | 1356763 A2 | 10/2003 |
| EP | 1356793 A2 | 10/2003 |
| EP | 0852481 B1 | 2/2004 |
| EP | 1401359 A2 | 3/2004 |
| EP | 1408850 A2 | 4/2004 |
| EP | 1233731 B1 | 12/2004 |
| EP | 1259194 B1 | 2/2005 |
| EP | 1214020 B1 | 3/2005 |
| EP | 1353420 B1 | 3/2005 |
| EP | 0955895 B1 | 8/2005 |
| EP | 1562522 A2 | 8/2005 |
| EP | 1014896 B1 | 11/2005 |
| EP | 1469797 B1 | 11/2005 |
| EP | 1600127 A2 | 11/2005 |
| EP | 1603493 A2 | 12/2005 |
| EP | 1621162 A2 | 2/2006 |
| EP | 1701668 A1 | 9/2006 |
| EP | 1600127 B1 | 11/2006 |
| EP | 1758523 A1 | 3/2007 |
| EP | 1255510 B1 | 4/2007 |
| EP | 1488735 B1 | 6/2007 |
| EP | 1143882 B1 | 12/2007 |
| EP | 1212989 B1 | 1/2008 |
| EP | 1653884 B1 | 6/2008 |
| EP | 1955643 A1 | 8/2008 |
| EP | 1978895 A2 | 10/2008 |
| EP | 1986579 A2 | 11/2008 |
| EP | 2000115 A2 | 12/2008 |
| EP | 1330213 B1 | 3/2009 |
| EP | 2055266 A2 | 5/2009 |
| EP | 2072027 A1 | 6/2009 |
| EP | 2078498 A1 | 7/2009 |
| EP | 1370201 B1 | 9/2009 |
| EP | 2133039 A1 | 12/2009 |
| EP | 2138132 A2 | 12/2009 |
| EP | 2258312 A1 | 12/2010 |
| EP | 2260796 A2 | 12/2010 |
| EP | 2260797 A2 | 12/2010 |
| EP | 2260798 A2 | 12/2010 |
| EP | 2340075 A2 | 7/2011 |
| EP | 2476394 A1 | 7/2012 |
| EP | 2526895 A1 | 11/2012 |
| EP | 2526898 A1 | 11/2012 |

(56) References Cited

FOREIGN PATENT DOCUMENTS

| | | | |
|---|---|---|---|
| EP | 2526899 A1 | 11/2012 |
| EP | 2529696 A1 | 12/2012 |
| EP | 2529697 A1 | 12/2012 |
| EP | 2529698 A1 | 12/2012 |
| EP | 2529699 A1 | 12/2012 |
| EP | 2537487 A1 | 12/2012 |
| EP | 3034014 A2 | 6/2016 |
| FR | 2783217 A1 | 3/2000 |
| FR | 2788217 A1 | 7/2000 |
| FR | 2815844 A1 | 5/2002 |
| FR | 2815844 B1 | 1/2003 |
| FR | 2828091 A1 | 2/2003 |
| GB | 2056023 A | 3/1981 |
| GB | 2083362 A | 3/1982 |
| GB | 2056023 B | 8/1983 |
| GB | 2433700 A | 7/2007 |
| GB | 2433700 B | 12/2007 |
| JP | H11332997 A | 12/1999 |
| JP | 2004154164 A | 6/2004 |
| NL | 1017275 C2 | 8/2002 |
| SU | 1271508 A1 | 11/1986 |
| WO | WO-9209247 A1 | 6/1992 |
| WO | WO-9511055 A1 | 4/1995 |
| WO | WO-9529640 A1 | 11/1995 |
| WO | WO-9639942 A1 | 12/1996 |
| WO | WO-9724989 A1 | 7/1997 |
| WO | WO-9814138 A1 | 4/1998 |
| WO | WO-9817202 A1 | 4/1998 |
| WO | WO-9829057 A1 | 7/1998 |
| WO | WO-9853761 A1 | 12/1998 |
| WO | WO-9904728 A1 | 2/1999 |
| WO | WO-9912483 A1 | 3/1999 |
| WO | WO-9913802 A1 | 3/1999 |
| WO | WO-9953864 A1 | 10/1999 |
| WO | WO-9953866 A1 | 10/1999 |
| WO | WO-9955255 A1 | 11/1999 |
| WO | WO-9956665 A1 | 11/1999 |
| WO | WO-0006052 A1 | 2/2000 |
| WO | WO-9953866 A8 | 2/2000 |
| WO | WO-0018303 A1 | 4/2000 |
| WO | WO-0021464 A1 | 4/2000 |
| WO | WO-0030565 A1 | 6/2000 |
| WO | WO-0041525 A2 | 7/2000 |
| WO | WO-0041652 A1 | 7/2000 |
| WO | WO-0041852 A1 | 7/2000 |
| WO | WO-0044313 A1 | 8/2000 |
| WO | WO-0047136 A1 | 8/2000 |
| WO | WO-0047139 A1 | 8/2000 |
| WO | WO-0062714 A1 | 10/2000 |
| WO | WO-0062716 A1 | 10/2000 |
| WO | WO-0117496 A1 | 3/2001 |
| WO | WO-0121076 A1 | 3/2001 |
| WO | WO-0121097 A2 | 3/2001 |
| WO | WO-0121107 A1 | 3/2001 |
| WO | WO-0121110 A1 | 3/2001 |
| WO | WO-0121244 A1 | 3/2001 |
| WO | WO-0135870 A1 | 5/2001 |
| WO | WO-0149213 A2 | 7/2001 |
| WO | WO-0154625 A1 | 8/2001 |
| WO | WO-0162189 A1 | 8/2001 |
| WO | WO-0164137 A1 | 9/2001 |
| WO | WO-0176510 A2 | 10/2001 |
| WO | WO-0211646 A1 | 2/2002 |
| WO | WO-0222054 A1 | 3/2002 |
| WO | WO-0236048 A1 | 5/2002 |
| WO | WO-0241789 A2 | 5/2002 |
| WO | WO-0247575 A2 | 6/2002 |
| WO | WO-0121110 A9 | 8/2002 |
| WO | WO-0241789 A3 | 8/2002 |
| WO | WO-0121103 A9 | 10/2002 |
| WO | WO-02076348 A1 | 10/2002 |
| WO | WO-02078348 A2 | 10/2002 |
| WO | WO-02092257 A1 | 11/2002 |
| WO | WO-0247575 A3 | 12/2002 |
| WO | WO-03003943 A2 | 1/2003 |
| WO | WO-03003949 A2 | 1/2003 |
| WO | WO-03011195 A2 | 2/2003 |
| WO | WO-03047468 A1 | 6/2003 |
| WO | WO-03003943 A3 | 11/2003 |
| WO | WO-03094797 A1 | 11/2003 |
| WO | WO-03003949 A3 | 1/2004 |
| WO | WO-2004019825 A1 | 3/2004 |
| WO | WO-2004028399 A2 | 4/2004 |
| WO | WO-2004082527 A2 | 9/2004 |
| WO | WO-2004089250 A1 | 10/2004 |
| WO | WO-2004089253 A1 | 10/2004 |
| WO | WO-2004091455 A2 | 10/2004 |
| WO | WO-2005004753 A1 | 1/2005 |
| WO | WO-2004091455 A3 | 2/2005 |
| WO | WO-2005046525 A1 | 5/2005 |
| WO | WO-2005046528 A1 | 5/2005 |
| WO | WO-2005062980 A2 | 7/2005 |
| WO | WO-2005065200 A2 | 7/2005 |
| WO | WO-2005082578 A1 | 9/2005 |
| WO | WO-2005096993 A1 | 10/2005 |
| WO | WO-2005104957 A2 | 11/2005 |
| WO | WO-2006005015 A2 | 1/2006 |
| WO | WO-2006007401 A2 | 1/2006 |
| WO | WO-2006009690 A1 | 1/2006 |
| WO | WO-2006014233 A2 | 2/2006 |
| WO | WO-2006026371 A1 | 3/2006 |
| WO | WO-2006044679 A1 | 4/2006 |
| WO | WO-2006054107 A2 | 5/2006 |
| WO | WO-2006063199 A2 | 6/2006 |
| WO | WO-2006076890 A1 | 7/2006 |
| WO | WO-2006086135 A2 | 8/2006 |
| WO | WO-2006088712 A1 | 8/2006 |
| WO | WO-2006089517 A1 | 8/2006 |
| WO | WO-2006093795 A1 | 9/2006 |
| WO | WO-2006116558 A2 | 11/2006 |
| WO | WO-2006117016 A1 | 11/2006 |
| WO | WO-2006124649 A2 | 11/2006 |
| WO | WO-2006127089 A1 | 11/2006 |
| WO | WO-2006127765 A1 | 11/2006 |
| WO | WO-2006135551 A2 | 12/2006 |
| WO | WO-2006135831 A1 | 12/2006 |
| WO | WO-2006136930 A1 | 12/2006 |
| WO | WO-2006138173 A2 | 12/2006 |
| WO | WO-2007009117 A1 | 1/2007 |
| WO | WO-2007021708 A1 | 2/2007 |
| WO | WO-2007033093 A2 | 3/2007 |
| WO | WO-2007053243 A2 | 5/2007 |
| WO | WO-2007059252 A1 | 5/2007 |
| WO | WO-2007030825 A3 | 6/2007 |
| WO | WO-2007071436 A2 | 6/2007 |
| WO | WO-2007076463 A2 | 7/2007 |
| WO | WO-2007130537 A1 | 11/2007 |
| WO | WO-2006007401 A3 | 1/2008 |
| WO | WO-0121097 A3 | 3/2008 |
| WO | WO-2008028569 A1 | 3/2008 |
| WO | WO-2008031103 A2 | 3/2008 |
| WO | WO-2008035337 A2 | 3/2008 |
| WO | WO-2008047354 A2 | 4/2008 |
| WO | WO-2008070797 A2 | 6/2008 |
| WO | WO-2008089365 A2 | 7/2008 |
| WO | WO-2008091515 A2 | 7/2008 |
| WO | WO-2008097589 A1 | 8/2008 |
| WO | WO-2008125153 A1 | 10/2008 |
| WO | WO-2008138584 A1 | 11/2008 |
| WO | WO-2008150529 A1 | 12/2008 |
| WO | WO-2009002548 A1 | 12/2008 |
| WO | WO-2009024716 A2 | 2/2009 |
| WO | WO-2009029199 A1 | 3/2009 |
| WO | WO-2009042196 A2 | 4/2009 |
| WO | WO-2009045331 A1 | 4/2009 |
| WO | WO-2009045338 A1 | 4/2009 |
| WO | WO-2009061389 A2 | 5/2009 |
| WO | WO-2009081389 A1 | 7/2009 |
| WO | WO-2009091509 A1 | 7/2009 |
| WO | WO-2009094188 A2 | 7/2009 |
| WO | WO-2009111241 A2 | 9/2009 |
| WO | WO-2010008548 A2 | 1/2010 |
| WO | WO-2010112608 A1 | 10/2010 |
| WO | WO-2011044994 A1 | 4/2011 |

(56) References Cited

FOREIGN PATENT DOCUMENTS

| WO | WO-2012063228 A1 | 5/2012 |
|---|---|---|
| WO | WO-2013037805 A1 | 3/2013 |
| WO | WO-2013075215 A1 | 5/2013 |
| WO | WO-2013082454 A1 | 6/2013 |
| WO | WO-2013096541 A1 | 6/2013 |
| WO | WO-2013128436 A1 | 9/2013 |
| WO | WO-2014121280 A2 | 8/2014 |
| WO | WO-2015036617 A2 | 3/2015 |
| WO | WO-2015191839 A1 | 12/2015 |
| WO | WO-2017195125 A1 | 11/2017 |

OTHER PUBLICATIONS

Babaliaros V., et al., "State of the Art Percutaneous Intervention for the Treatment of Valvular Heart Disease: A Review of the Current Technologies and Ongoing Research in the Field of Percutaneous Valve Replacement and Repair," Cardiology, 2007, vol. 107, pp. 87-96.
Bailey S.R., "Percutaneous Expandable Prosthetic Valves," Textbook of Interventional Cardiology, Second Edition, W.B. Saunders Company, 1994, vol. 2, pp. 1268-1276.
Block P.C., et al., "Percutaneous Approaches to Valvular Heart Disease," Current Cardiology Reports, Mar. 2005, vol. 7(2), pp. 108-113.
Bonhoeffer P., et al., "Percutaneous Insertion of the Pulmonary Valve," Journal of the American College of Cardiology, May 15, 2002, vol. 39, pp. 1664-1669.
Bonhoeffer P., et al., "Percutaneous Replacement of Pulmonary Valve in a Right-Ventricle to Pulmonary-Artery Prosthetic Conduit with Valve Dysfunction," Lancet, Oct. 2000, vol. 356, pp. 1403-1405.
Bonhoeffer P., et al., "Transcatheter Implantation of a Bovine Valve in Pulmonary Position: A Lamb Study," Circulation, Aug. 15, 2000, vol. 102, pp. 813-816.
Boudjemline Y., et al., "Images in Cardiovascular Medicine: Percutaneous Aortic Valve Replacement in Animals," Circulation, United States, Mar. 16, 2004, vol. 109, p. e161.
Boudjemline Y., et al., "Is Percutaneous Implantation of a Bovine Venous Valve in the Inferior Vena Cava a Reliable Technique to Treat Chronic Venous Insufficiency Syndrome?," Medical Science Monitor, Poland, Mar. 2004, vol. 10(3), pp. BR61-BR66.
Boudjemline Y., et al., "Off-Pump Replacement of the Pulmonary Valve in Large Right Ventricular Outflow Tracts: A Hybrid Approach," Journal of Thoracic and Cardiovascular Surgery, United States, Apr. 2005, vol. 129(4), pp. 831-837.
Boudjemline Y., et al., "Percutaneous Aortic Valve Replacement: Will We Get There?," Heart, British Cardiac Society, England, Dec. 2001, vol. 86, pp. 705-706.
Boudjemline Y., et al., "Percutaneous Implantation of a Biological Valve in Aortic Position: Preliminary Results in a Sheep Study," European Heart Journal, Sep. 1-5, 2001, vol. 22, p. 630.
Boudjemline Y., et al., "Percutaneous Implantation of a Biological Valve in the Aorta to Treat Aortic Valve Insufficiency—A Sheep Study," Medical Science Monitor, Apr. 12, 2002, vol. 8(4), pp. BR113-BR116.
Boudjemline Y., et al., "Percutaneous Implantation of a Valve in the Descending Aorta in Lambs," European Heart Journal, Jul. 2002, vol. 23, pp. 1045-1049.
Boudjemline Y., et al., "Percutaneous Pulmonary Valve Replacement in a Large Right Ventricular Outflow Tract: An Experimental Study," Journal of the American College of Cardiology, Mar. 17, 2004, vol. 43(6), pp. 1082-1087.
Boudjemline Y., et al., "Percutaneous Valve Insertion: A New Approach?," Journal of Thoracic and Cardiovascular Surgery, United States, Mar. 2003, vol. 125(3), pp. 741-742.
Boudjemline Y., et al., "Stent Implantation Combined with a Valve Replacement to Treat Degenerated Right Ventricle to Pulmonary Artery Prosthetic Conduits," European Heart Journal, Sep. 2001, vol. 22, p. 355.
Boudjemline Y., et al., "Steps Toward Percutaneous Aortic Valve Replacement," Circulation, Feb. 12, 2002, vol. 105, pp. 775-778.
Boudjemline Y., et al., "The Percutaneous Implantable Heart Valve," Progress in Pediatric Cardiology, Ireland, 2001, vol. 14, pp. 89-93.
Boudjemline Y., et al., "Transcatheter Reconstruction of the Right Heart," Cardiology in the Young, England, 2003, vol. 13, pp. 308-311.
Coats L., et al., "The Potential Impact of Percutaneous Pulmonary Valve Stent Implantation on Right Ventricular Outflow Tract Re-Intervention," European Journal of Cardio-Thoracic Surgery, England, Apr. 2005, vol. 27, pp. 536-543.
Cribier A., et al., "Percutaneous Transcatheter Implantation of an Aortic Valve Prosthesis for Calcific Aortic Stenosis: First Human Case Description," Circulation, 2002, vol. 106, pp. 3006-3008.
Davidson M.J., et al., "Percutaneous Therapies for Valvular Heart Disease," Cardiovascular Pathology, Jan. 2006, vol. 15, pp. 123-129.
Grube E., et al., "First Report on a Human Percutaneous Transluminal Implantation of a Self-Expanding Valve Prosthesis for Interventional Treatment of Aortic Valve Stenosis," Valvular Heart Disease, Catheterization and Cardiovascular Interventions, 2005, vol. 66, pp. 465-469.
Grube E., et al., "Percutaneous Implantation of the Core Valve Self-Expanding Valve Prosthesis in High-Risk Patients With Aortic Valve Disease: The Siegburg First-in-Man Study," American Heart Association, Circulation, 2006, vol. 114, pp. 1616-1624.
Hanzel G.S., et al., "Complications of Percutaneous Aortic Valve Replacement: Experience with the Cribier-Edwards TM Percutaneous Heart Valve," EuroIntervention Supplements, 2006, vol. 1(A), pp. A3-A8.
Ho P.C., "Percutaneous Aortic Valve Replacement: A Novel Design of the Delivery and Deployment System," Minimally Invasive Therapy, 2008, vol. 17(3), pp. 190-194.
Huber C.H., et al., "Direct-Access Valve Replacement: A Novel Approach for Off-Pump Valve Implantation Using Valved Stents," Journal of the American College of Cardiology, Jul. 19, 2005, vol. 46(2), pp. 366-370.
Huber C.H., et al., "Do Valved Stents Compromise Coronary Flow?," European Journal of Cardio-thoracic Surgery, Jan. 23, 2004, vol. 25, pp. 754-759.
International Search Report and Written Opinion for International Application No. PCT/IB2018/053646, mailed Feb. 22, 2019, 9 pages.
Khambadkone S., et al., "Nonsurgical Pulmonary Valve Replacement: Why, When, and How?," Catheterization and Cardiovascular Interventions, United States, Jul. 2004, vol. 62, pp. 401-408.
Khambadkone S., et al., "Percutaneous Implantation of Pulmonary Valves," Expert Review of Cardiovascular Therapy (England), Nov. 2003, vol. 1(4), pp. 541-548.
Khambadkone S., et al, "Percutaneous Pulmonary Valve Implantation: Early and Medium Term Results," Circulation, Oct. 28, 2003, vol. 108(17), p. IV-375.
Khambadkone S., et al., "Percutaneous Pulmonary Valve Implantation: Impact of Morphology on Case Selection," Circulation, Oct. 28, 2003, vol. 108(17), pp. IV-642-IV-643.
Lutter G., et al., "Percutaneous Aortic Valve Replacement: An Experimental Study. I. Studies on Implantation," Journal of Thoracic and Cardiovascular Surgery, Apr. 2002, vol. 123(4), pp. 768-776.
Lutter G., et al., "Percutaneous Valve Replacement: Current State and Future Prospects," Annals of Thoracic Surgery, Netherlands, Dec. 2004, vol. 78, pp. 2199-2206.
Ma L., et al., "Double-Crowned Valved Stents for Off-Pump Mitral Valve Replacement," European Journal of Cardio-Thoracic Surgery, Jun. 13, 2005, vol. 28(2), pp. 194-199.
Medtech Insight, "New Frontiers in Heart Valve Disease," Aug. 2005, vol. 7(8), 38 pages.
Palacios I.F., "Percutaneous Valve Replacement and Repair: Fiction or Reality?," Journal of American College of Cardiology, Oct. 2004, vol. 44(8), pp. 1662-1663.
Pavcnik D., et al., "Aortic and Venous Valve for Percutaneous Insertion," Minimally Invasive Therapy & Allied Technologies, Jan. 2000, vol. 9(3/4), pp. 287-292.

(56) References Cited

OTHER PUBLICATIONS

Pelton A.R., et al., "Medical Uses of Nitinol," Materials Science Forum, Jan. 2000, vol. 327-328, pp. 63-70.
Roth M., "Old Metal Heart Valve Did its Job for 42 Years," Pittsburgh Post-Gazette, Mar. 5, 2008, 3 pages.
Ruiz C.E., "Transcatheter Aortic Valve Implantation and Mitral Valve Repair: State of the Art," Pediatric Cardiology, Jun. 2005, vol. 26(3), pp. 289-294.
Saliba Z., et al., "Treatment of Obstructions of Prosthetic Conduits by Percutaneous Implantation of Stents," Archives Des Maladies Du Coeur Et Des Vaisseaux, May 1999, pp. 591-596.
Stassano P., et al., "Mid-term Results of the Valve-on-Valve Technique for Bioprosthetic Failure," European Journal of Cardiothoracic Surgery, Oct. 2000, vol. 18, pp. 453-457.
Webb J.G., et al., "Percutaneous Aortic Valve Implantation Retrograde from the Femoral Artery," Circulation, American Heart Association, Feb. 14, 2006, vol. 113, pp. 842-850.

\* cited by examiner

DEVICE FOR THE IN-SITU DELIVERY OF HEART VALVE PROSTHESIS

CROSS REFERENCE TO RELATED APPLICATIONS

This application is a national stage application of PCT/IB2018/053646 filed May 23, 2018, which is herein incorporated by reference in its entirety.

TECHNICAL FIELD

The present disclosure relates to devices for the in-situ delivery of heart valve prostheses.

BACKGROUND

Expandable heart valve prostheses typically include an expandable and collapsible anchoring structure or armature, capable of supporting and fixing the valve prosthesis in the implantation position, and prosthetic valve elements, generally in the form of leaflets or flaps, which are stably connected to the anchoring structure and able to regulate blood flow.

These expandable prosthetic valves enable implantation using traditional (surgical), minimally invasive, or sutureless techniques. Exemplary applications for such an expandable valve prosthesis include aortic and pulmonary valve replacement.

Certain heart valve prostheses feature an armature that requires a delivery instrument with multiple deployment elements in order for it to be kept in a radially contracted condition properly, as well as to be properly deployed at the implantation site, i.e. without threatening the safety and life of the patient.

SUMMARY

One exemplary heart valve prosthesis featuring an expandable/collapsible armature is disclosed in EP 1 690 515 B1 in the name of the same Applicant, and another is disclosed in PCT application no. PCT/IB2018/053640 filed on even date herewith in the name of the same applicant, both of which are hereby incorporated by reference herein.

A preferred solution for delivery of such prostheses consists in loading the same onto the carrier portion of a delivery instrument featuring two deployment elements slidable over a hub. Each deployment element may be associated to—respectively—a proximal or a distal portion of the prosthesis armature (depending on a variety of reasons such as the delivery approach—antegrade or retrograde—and/or the armature features) and is operated to release the armature typically in a staged fashion. Control of the deployment elements is generally provided at a handle of the instrument by rotary or sliding drive members. The deployment process may be generally susceptible of requesting a control pattern that takes into account specific circumstances of the deployment itself, such as a slow action at a stage when the prosthesis has just entered the implantation site and/or when the prosthesis is being positioned to match the specific anatomy of the site, and a fast action when optimal positioning has been reached and/or deployment has progressed nearly to completion, so as to complete release of the prosthesis by taking the least possible time, and accordingly minimize the window for possible incidents or inconveniences. This is generally not available to prior art delivery instruments, as the drive members thereof typically do not provide for a variable control pattern of the deployment elements.

In a first example of a deployment instrument for expandable heart valve prostheses, the deployment instrument includes a shaft having a longitudinal axis, a handle at a first end of the shaft, and a carrier portion at a second end of the shaft. The carrier portion is configured for holding an expandable heart valve prosthesis in a radially collapsed condition for delivery to the implantation site. The carrier portion includes a hub fixed to the handle via the shaft, a first deployment element, and a second deployment element. Each of said first deployment element and second deployment element is configured to hold a corresponding portion of an expandable heart valve prosthesis in a radially collapsed condition. The handle comprises a drive member including a first drive feature and a second drive feature. The first deployment element of the carrier portion is connected to a first axially movable element engaging said first drive feature of the drive member. The second deployment element of the carrier portion is connected to a second axially movable element engaging said second drive feature of the drive member. Where upon operation of the drive member the first drive feature is configured to axially displace the first deployment element in a first direction, and the second drive feature is configured to axially displace the second deployment element in a second direction, said first direction and said second direction being opposite to one another. Further, the second axially movable member includes a first portion and a second portion, the first portion engaging the second drive feature, and the second portion being axially movable relative to the first portion to provide an axial displacement of the second deployment element in the second direction independently of the drive member.

In a second example according to the first example, wherein the first end of the shaft is a proximal end, and the second end of the shaft is a distal end.

In a third example according to the first example or the second example, wherein the first direction is a distal direction, and the second direction is a proximal direction.

In a fourth example according to the first example, wherein said first drive feature comprises a first threaded portion, and said second drive feature comprises a second threaded portion.

In a fifth example according to the fourth example, wherein said drive member is a rotary drive member comprising a knob and a stem, the first drive feature being provided on a first surface of the stem, and the second drive feature being provided on a second surface of the stem.

In a sixth example according to the fifth example, wherein said stem is a hollow member, said first drive feature being provided on an inner surface of the stem, and said second drive feature being provided on an outer surface of the stem.

In a seventh example according to the first example, wherein the first portion and the second portion of the second axially movable element are partly overlapping and slidably coupled to one another.

In an eighth example according to the seventh example, the second axially movable element including an elastic element biasing the second portion away from the first portion.

In a ninth example according to any one of the first example, the seventh example, and the eighth example, wherein the first portion includes an annular portion wherefrom a first pair of diametrically opposite axial extensions protrude, and an internal thread provided on the cylindrical inner surfaces of the axial extensions of the first pair and the annular member. The internal thread being configured to engage the second drive feature. Where the axial extensions merge at a flange wherefrom a second pair of diametrically opposite axial extensions departs axially away from the first pair of axial extensions.

In a tenth example according to the ninth example, wherein the axial extensions of the second pair are arranged at a location at right angle relative to the axial extensions of the first pair.

In an eleventh example according to the ninth example or the tenth example, wherein each axial extension of the second pair includes a through axial slot, the axial extensions of the second pair being separated by a pair of axial grooves.

In a twelfth example according to any one of the ninth to eleventh examples, wherein the second portion of the second axially movable element includes an annular member wherefrom a third pair of diametrically opposite axial extensions protrude.

In a thirteenth example according to the twelfth example, wherein the axial extensions of the third pair have the same position as the axial extensions in the second pair, and are each provided with a radially protruding plug. Where a pair of radially protruding teeth, diametrically opposite, extend from an inner surface of the annular portion and inwardly of the same, while a pair diametrically opposite guide fingers extend axially at said annular portion at positions at right angles relative to those of the radially protruding teeth. Also, wherein the guide fingers are aligned with a corresponding through axial slot and slidably engage the same, while the teeth are aligned with the grooves separating the axial extensions of the second pair, and are slidable therethrough.

In a fourteenth example according to any one of the previous examples, wherein the shaft has a layered structure.

In a fifteenth example according to the fourteenth example, wherein the shaft includes a first shaft member as middle layer, a second shaft member as outer layer, and a rod or shaft member as a core. The first shaft member connects the hub of the carrier portion to the handle, and the second shaft member connects the second deployment element to the second axially movable element. The rod or shaft member connects the first deployment element to the first axially movable member.

In a sixteenth example according to the fifteenth example, wherein the second shaft member is engaged by the axial extensions of the third pair.

A seventeenth example of a deployment instrument for expandable heart valve prostheses including:
 a shaft having a longitudinal axis;
 a handle at a first end of the shaft; and
 a carrier portion at a second end of the shaft, the carrier portion configured for holding an expandable heart valve prosthesis in a radially collapsed condition for delivery to the implantation site, wherein:
 the carrier portion includes a hub coupled to the handle via the shaft, a first deployment element and a second deployment element, each of said first deployment element and second deployment element configured to hold a corresponding portion of an expandable heart valve prosthesis in a radially collapsed condition,
 the handle comprises a drive member including a first drive feature configured to axially displace the first deployment element in a first direction and a second drive feature configured to axially displace the second deployment element in a second, opposite, direction.

In an eighteenth example according to the seventeenth example the second deployment element is coupled to the second drive feature by a second axially movable member that includes a first portion and a second portion, the first portion engaging the second drive feature, and the second portion being independently axially movable relative to the first portion.

While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

BRIEF DESCRIPTION OF THE FIGURES

The disclosure will now be provided with reference to the attached drawings, given purely by way of non-limiting example, wherein.

While the disclosure is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

DETAILED DESCRIPTION

Figure 1:
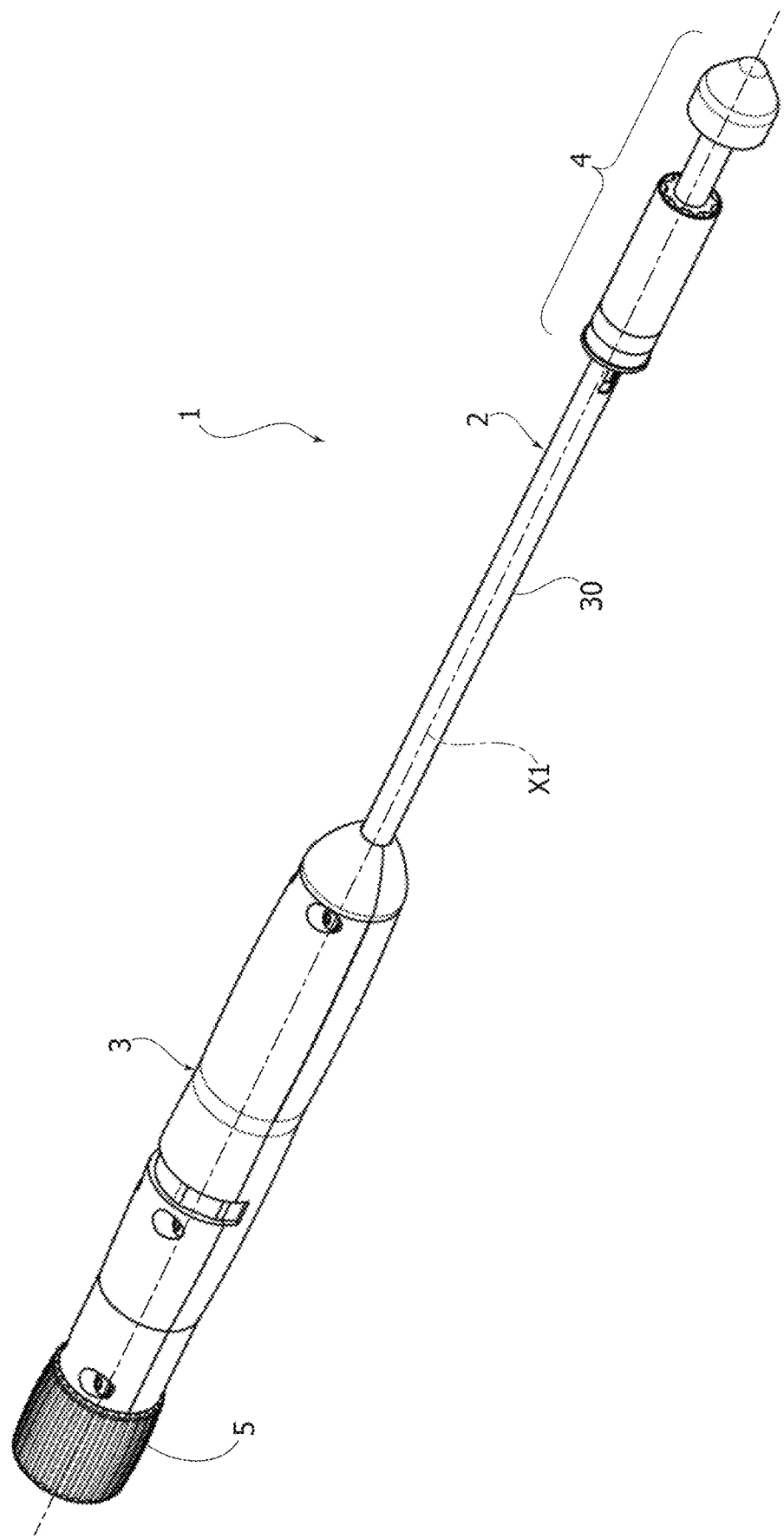
FIG. 1 is a perspective view of a deployment instrument, according to embodiments of the disclosure.

Reference number 1 in FIG. 1 applies to a deployment instrument for expandable heart valve prostheses according to various embodiments of this disclosure.

In embodiments, such as that exemplified in the figures, the deployment instrument 1 includes:
 a shaft 2 having a longitudinal axis X1;
 a handle 3 at a first end of the shaft 2; and
 a carrier portion 4 at a second end of the shaft 2.

The carrier portion 4 is configured for holding an expandable heart valve prosthesis in a radially collapsed condition for delivery to the implantation site.

Figure 2A:
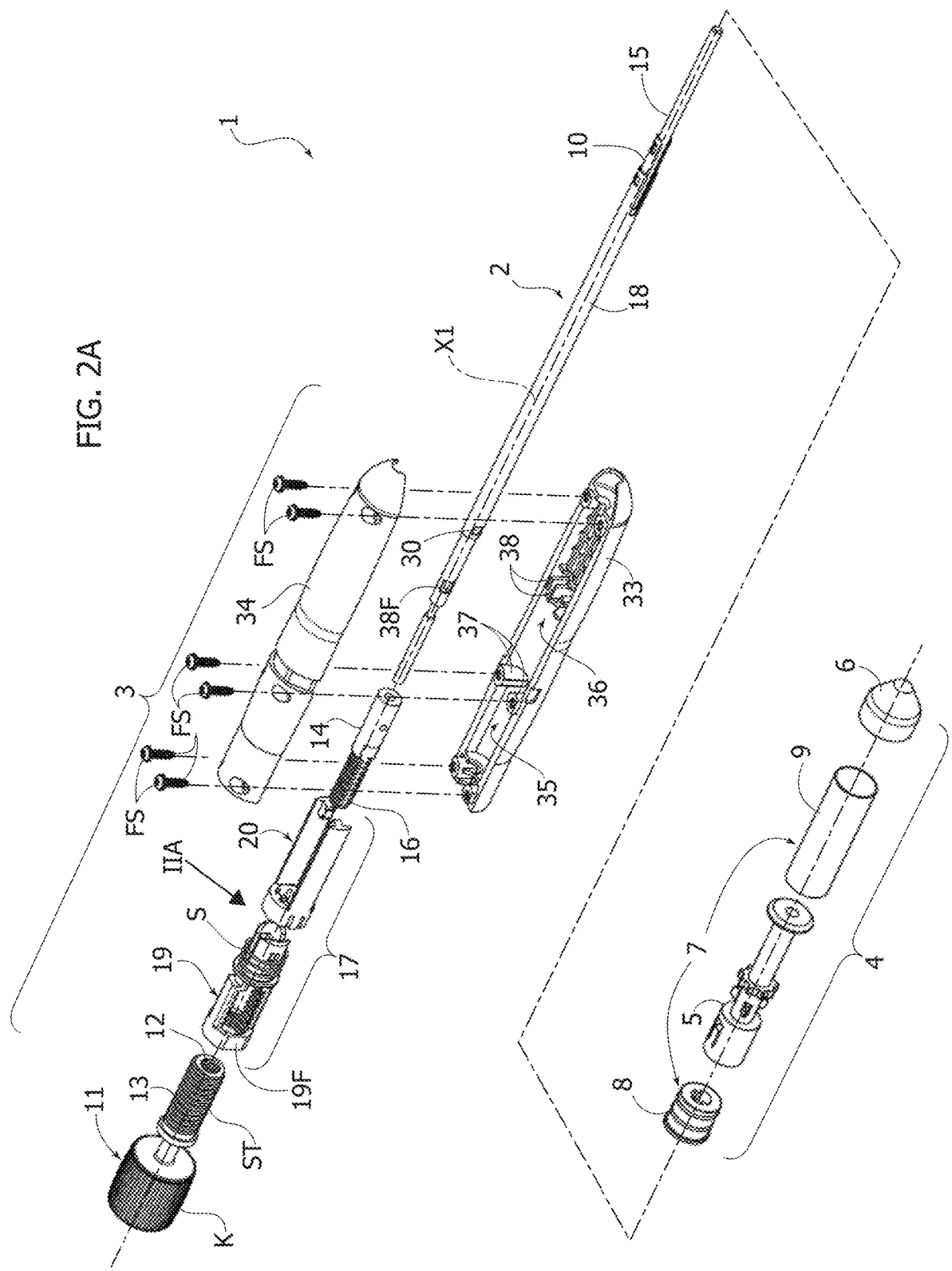
FIG. 2A is an exploded perspective view of the instrument of FIG. 1, according to embodiments of the disclosure.

Referring now to FIG. 2A, in embodiments the carrier portion 4 may include a hub 5 fixed to the handle 3 via the shaft 2, a first deployment element 6, and a second deployment element 7. Each of the first deployment element 6 and second deployment element 7 is configured to hold a corresponding portion of an expandable heart valve prosthesis in a radially collapsed condition.

In embodiments, the first deployment element 6 may be provided as a cup member featuring an ogee-like shape, preferably with a blunt end to avoid damaging to the patient's tissues and vasculature.

The second deployment element 7 may be—instead—provided as a sheath member including a plug 8 and a sheath 9 fitted onto the plug 8 (e.g. by interference fitting, or else thermally bonded thereto).

The hub 5 is fixed to the handle 3 via a first shaft member 10 provided as a tubular element (preferably thin walled) that attaches at one end thereof to the hub, and at another end thereof at the handle 3. Attachment may be provided, e.g., by snap fitting—as visible in the figures—by providing openings at the end of the shaft member 10 configured to be engaged by resilient protrusions on the hub 5 and the handle 3 respectively.

In embodiments, the handle comprises a drive member 11 including a first drive feature 12 and a second drive feature 13. The drive member 11 may include a knob K for operation by the practitioner, and a hollow stem ST featuring the first drive feature on an inner surface, and the second drive feature on an outer surface.

In other embodiments, depending on how the drive feature is made and operates, both drive features may be provided on one and a same surface of the stem ST, or else on concentric surfaces with different diameters.

In some embodiments, such as that visible in the figures, the drive features 12, 13 may be provided as threaded portions of the stem AT, wherein the drive feature 12 is an internal thread provided on an inner cylindrical surface of the stem, while the drive feature 13 is an external thread provided on an outer cylindrical surface of the stem ST.

In some embodiments, the drive features 12, 13 may be provided as a cam track that develops on the respective surface of the stem ST (such as a drum cam). In other embodiments, depending on the needs, a mixed configuration may be adopted featuring a thread for one of the drive features 12, 13 and a cam track for the other of the drive features 12, 13. In some embodiments, any profile capable of transforming its motion (generally a rotary motion) into another motion (generally an axial motion) of another member that engages with the profile may be regarded as a drive feature within the context of the present disclosure.

Whatever the embodiments of the drive features 12, 13 the same are arranged so that upon operation of the drive member 11 the first drive feature 12 is configured to axially displace the first deployment element 6 (along the axis X1) in a first direction, and the second drive feature 13 is configured to axially displace the second deployment element 7 in a second direction, wherein the first direction and the second direction are opposite to one another. For example, when the drive features 12, 13 are provided both as threaded portions they will have opposite winding threads (i.e. a right thread and a left thread) so that a rotation of the drive member 11 will result in a distal displacement for one of the deployment elements and a proximal displacement in the other of the deployment elements and vice versa. When the drive features 12, 13 are provided as cam tracks, they will develop on the surface(s) of the stem ST of the drive member 11 e.g. with opposite slopes, so that—once again—a rotation of the drive member 11 will result in a distal displacement for one of the deployment elements and a proximal displacement in the other of the deployment elements and vice versa.

In embodiments such as that depicted in the figures the first deployment element 6 of the carrier portion 4 is connected to a first axially movable element 14 via a connecting rod or shaft member 15 that is slidably arranged into the shaft member 10. As visible in FIG. 2A, the rod of shaft member 15 has an axial extension higher than the axial extension of the shaft member 10. The first axially movable element 14 engages the first drive feature 12 of the drive member 11: specifically, in these embodiments the element 14 includes a stud 16 which may be threaded (externally threaded for the embodiment in the figures) or otherwise provided with a feature capable of mating with the drive feature 12. The stud 12 has two diametrically opposite flat sides serving as an anti-rotation feature, making the element 14 a non-rotating, axially displacing member.

The second deployment element 7 of the carrier portion 4 is connected to a second axially movable element 17 via a second shaft member 18 arranged around the first shaft member 10, and slidable relative thereto. In some embodiments, such as that depicted in the figures, the second shaft member 18 has the shortest axial length relative to the first shaft member and the rod or shaft member 15. The second axially movable element 17 engages the second drive feature 13 of the drive member 11 to drive the second deployment element 7.

The shaft 2 has therefore in embodiments a layered structure including the second shaft member 18 as outer layer, the first shaft member 10 as middle layer, and the rod or shaft member 15 as a core.

According to an advantageous aspect of the disclosure, the second axially movable member 17 includes a first portion 19 and a second portion 20, wherein the first portion 19 engages the second drive feature 13, while the second portion 20 is axially movable relative to the first portion 19 to provide an axial displacement of the second deployment element 7 in the second direction independently of the drive member 11.

Figure 2B:
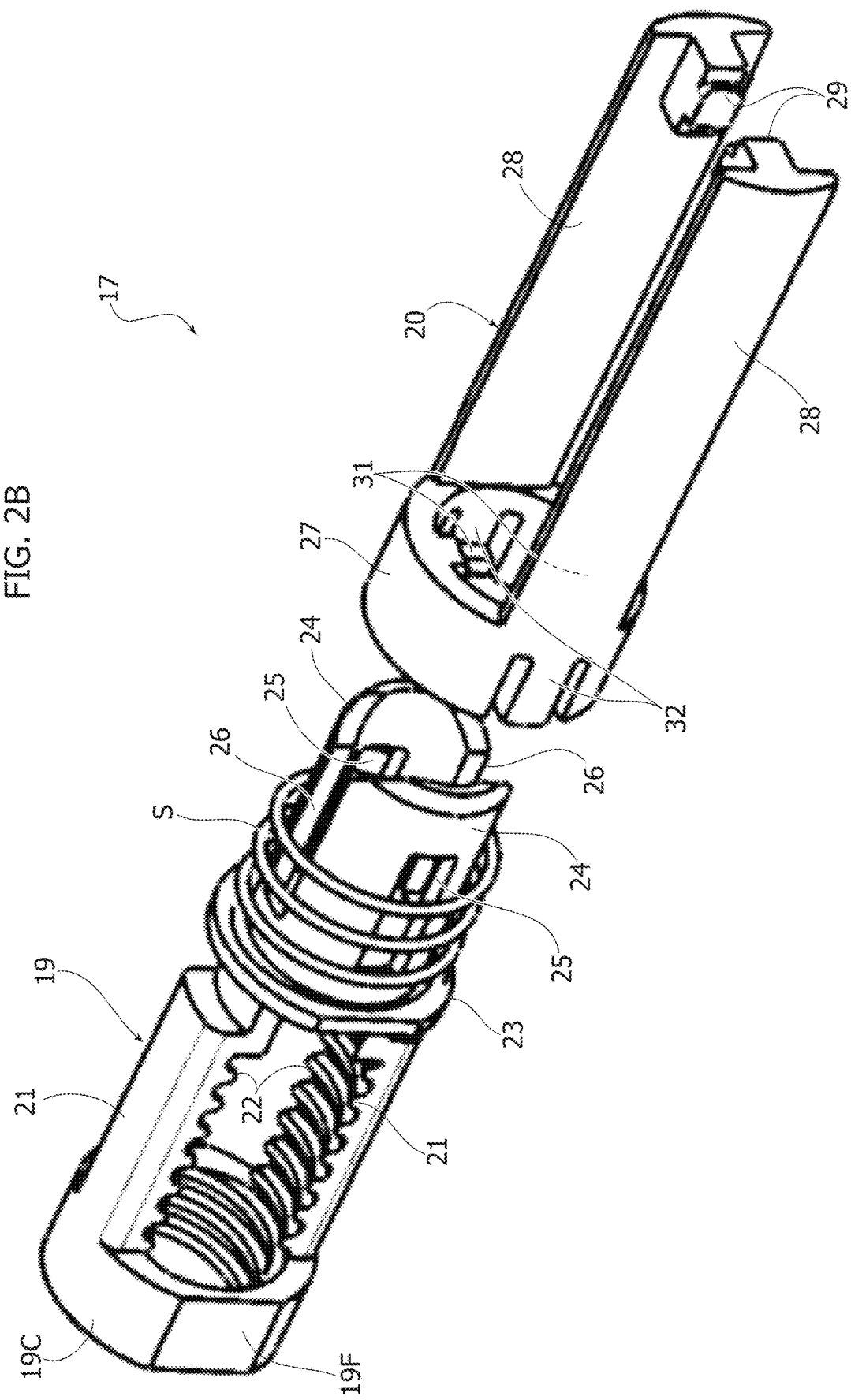
FIG. 2B is an exploded view of a sub-unit of the instrument of FIG. 2A, according to pointer IIA, according to embodiments of the disclosure.

More specifically, in embodiments as illustrated herein (FIG. 2B) the first portion 19 may include an annular portion 19C wherefrom a first pair of axial extensions 21, diametrically opposite, protrude.

An internal thread 22 is provided on the cylindrical inner surfaces of the extensions 21 and the annular member 19C, to engage the thread of the drive feature 13. Alternatively, these surfaces may be provided with one or more cam followers in the event that the drive feature 13 is provided as a cam track.

The extensions 21 merge at a flange 23 wherefrom a second pair of axial extension 24 departs axially away from the extensions 21. The axial extensions 24 are set once again at diametrically opposite positions, and cover an angular range wider than that covered by the extensions 21. This allows opening a pair of through axial slots 25 in the cylindrical wall of each extension 24 (the grooves 25 being diametrically opposite as well), as well as a pair of axial grooves 26 that separate the two axial extensions 24. Both the slots 25 and the grooves 26 serve as guide features for the portion 20.

Figure 5:
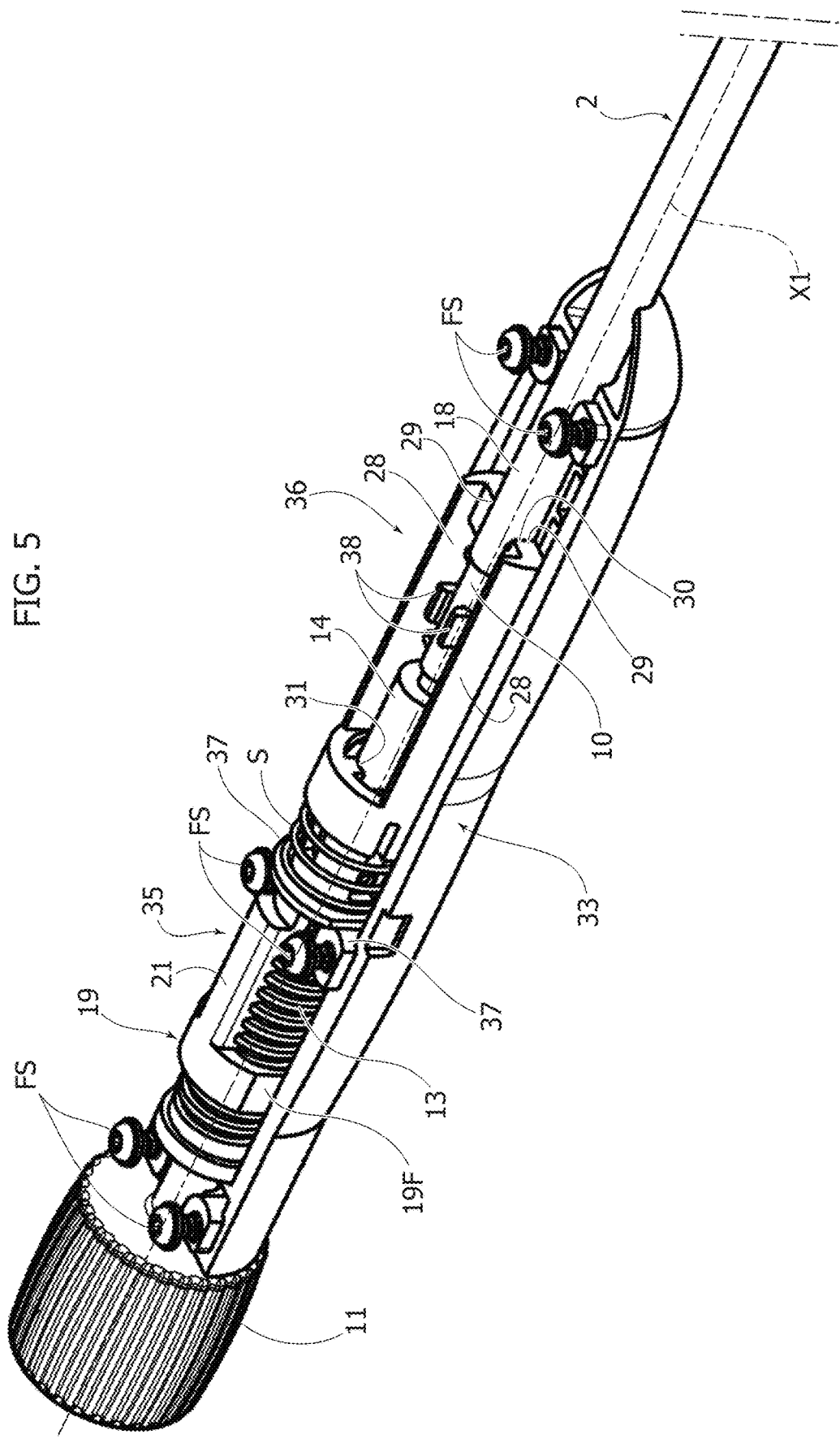
FIG. 5 is a perspective view corresponding to FIG. 4A, according to embodiments of the disclosure.

Coming to the latter, the portion 20, similarly to the portion 19, features an annular member 27 wherefrom a third pair of axial extensions 28 protrude. When the portions 19 and 20 are assembled, the extensions 28 will have, albeit on a larger diameter, the same angular position (diametrically opposite) as the extensions 24. The extensions 28 are each provided with a radially protruding plug 29 which is configured to snap fit into a respective opening 30 (FIGS. 2A, 5) provided at a proximal end of the shaft member 18, wherein proximal and distal are used herein relative to the handle 3 (proximal: towards the handle 3; distal: away from the handle 3).

A pair of radially protruding teeth 31, diametrically opposite, extend from an inner surface of the annular portion 27 and inwardly of the same, while a pair of guide fingers 32, which may be partly resilient, extend axially at diametrically opposite positions at right angles from those of the teeth 31. Specifically, the fingers 32 are aligned with the slots 25, while the teeth 31 are aligned with the grooves 26.

When assembled together, the second portion 20 partly overlaps the first portion 19 at the extensions 24, and specifically the annular member 27 is slidably mounted over the extensions 24 guided by the teeth 31 through the grooves 26, and the fingers 32 along the slots 25 (which also serve as a locking feature for the portion 20 relative to the portion 19 in the fully extended position on account of the engagement of the fingers 32 therein).

The fingers 32 are also provided with a radially protruding end portion (such as the plugs 29 at the ends of the extensions 28) that engages the slots 25 to prevent axial separation of the portions 19, 20, as well as to enable the portion 20 to be axially pulled by the portion 19 in a proximal direction. An elastic element S is fitted around the extensions 24 between the flange 23 and the annular member 27 and is configured to bias the first portion 19 and the second portion 20 away from one another, and specifically to bias the second portion 20 to an extended position wherein the radially protruding ends of the fingers 32 abut onto the distal ends of the slots 25.

Figure 3:
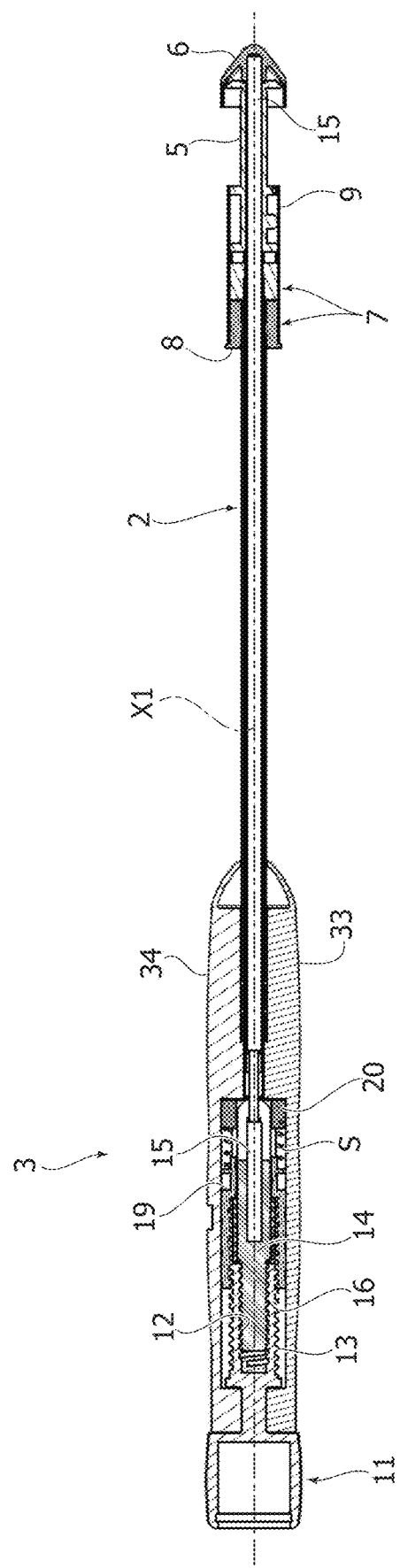
FIG. 3 is a longitudinal sectional view of the instrument of FIG. 1, according to embodiments of the disclosure.

Referring once again to FIG. 2A, and additionally to FIG. 3, the handle 3 includes a first shell 33 and a second shell 34 which, in embodiments, define respectively circumferential half of the overall shell of the handle 3. Each of the shells 33, 34 may advantageously incorporate guide and/or lock featured for the elements described previously, in order to ensure proper assembly and motion of the various components. Except where specified otherwise, in embodiments, the structure of the cradles 35, 36 is identical for each of the two elements 33, 34.

In some embodiments, the interior of the shells 33, 34 may be divided in a first cradle 35 and a second cradle 36, each intended to cradle a sub-set of the components previously identified in this disclosure. With reference to FIGS. 2A, 2B, 3, 4A, and 5, the first cradle 35 receives the drive member 11, particularly the stem ST, the first portion 19 of the second axially movable element 17 up to the end of the extensions 21 (the latter engaging the drive feature 13), and the stem 16 of the first axially movable member 14 that engages the drive feature 12 at the interior of the stem ST.

The cradle 35 is functionally separated from the cradle 36 by a pair of guide shoulders 37 which may act both as sockets for fastening screws FS that secure the shells 33 and 34 together, as well as axial guide surfaces for the extensions 21, which are accordingly prevented from rotating (and the portion 19 overall as well) while enabled to axially displace when the drive member 11 is operated. Anti-rotation features for the assembly of portions 19 and 20 is also provided by flat sides 19F of the portion 19 sliding along corresponding inner walls of the cradles 35, 36 (FIGS. 2A, 4A, 5), thus making the assembly of portions 19, 20, an axially displacing, non-rotating member.

Similar shoulders to the guide shoulders 37 may be provided at opposite ends of the shells 33, 34, as visible in the figures) to act both as sockets for the fastening screws FS, and as a guide for, respectively, the drive member 11 and the axially slidable portions of the shaft 2, such as the shaft member 18.

In embodiments, the cradle 36 in turn houses the remainder of the components of the handle 4, and specifically it houses the remainder of the portion 19 of the second axially movable element 17, the remainder of the first axially movable element, as well as proximal portions of the shaft 2 including a proximal portion of the rod or shaft member 15 fitting into the element 14, a proximal portion of the shaft member 10 fixing the hub 5 to the handle 3, and a proximal portion of the shaft member 18 engaging the plugs 29 on the extensions 28.

As to the shaft member 10, the same is secured to the shell 33 by way of a pair of tabs 38 extending along chordal planes parallel to one another and parallel to the axis X1, and configured to sit through side openings 38F (FIG. 2A, similar to the openings 30) to axially secure the shaft member 10 to the handle 3 (particularly to the shell 33) and the hub 5 too in the process. As to the tabs 38, in one embodiment they do not have a counterpart in the shell 34 primarily for reasons of assembly. In other embodiments the tabs 38 may be provided on the shell 34 only, while in yet other embodiments one tab 38 may be provided on the shell 33, the other on the shell 34.

Operation of the deployment instrument 1 according to embodiments of this disclosure will now be described.

The deployment instrument 1 is operable to delivery and release a heart valve prosthesis including a radially contractible/radially expandable armature and a prosthetic valve carried thereby to an implantation site.

Figure 4A:
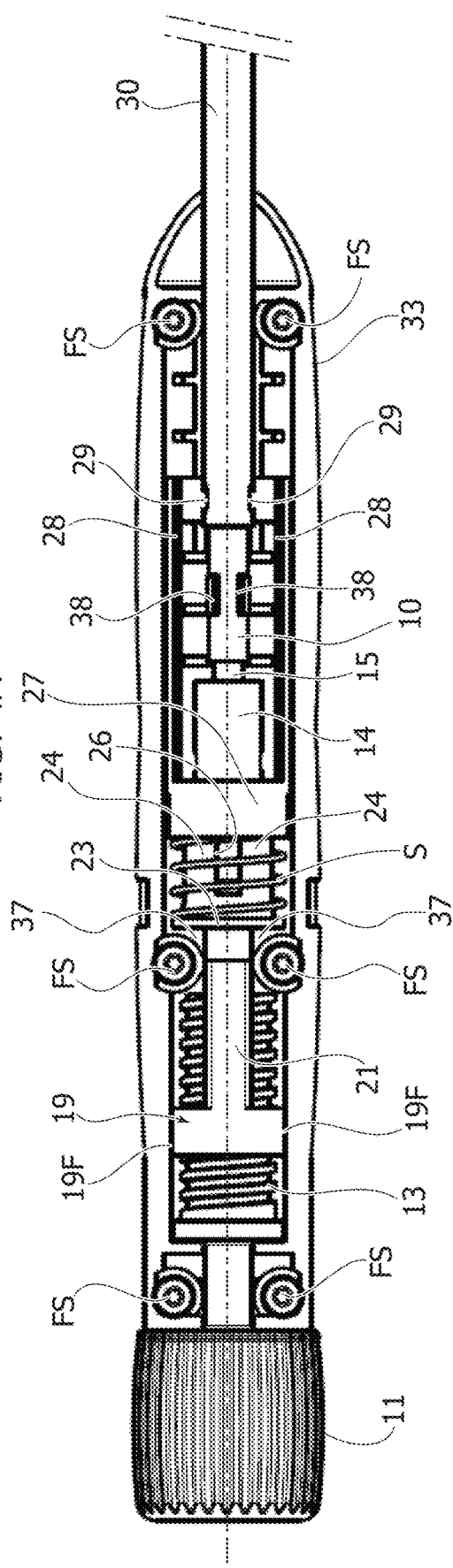
FIG. 4A is a partly disassembled view of an end portion of the instrument, according to embodiments of the disclosure.
Figure 4B:
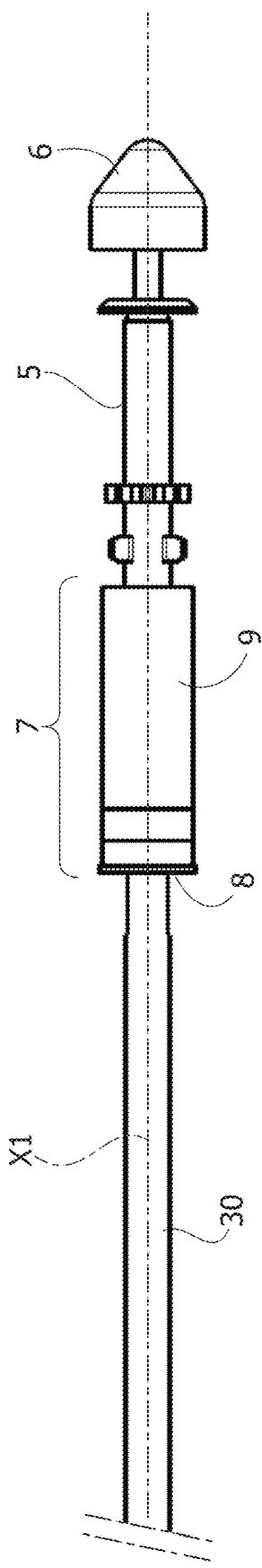
FIG. 4B is a view of an opposite end portion of the instrument, according to embodiments of the disclosure.
Figure 9:
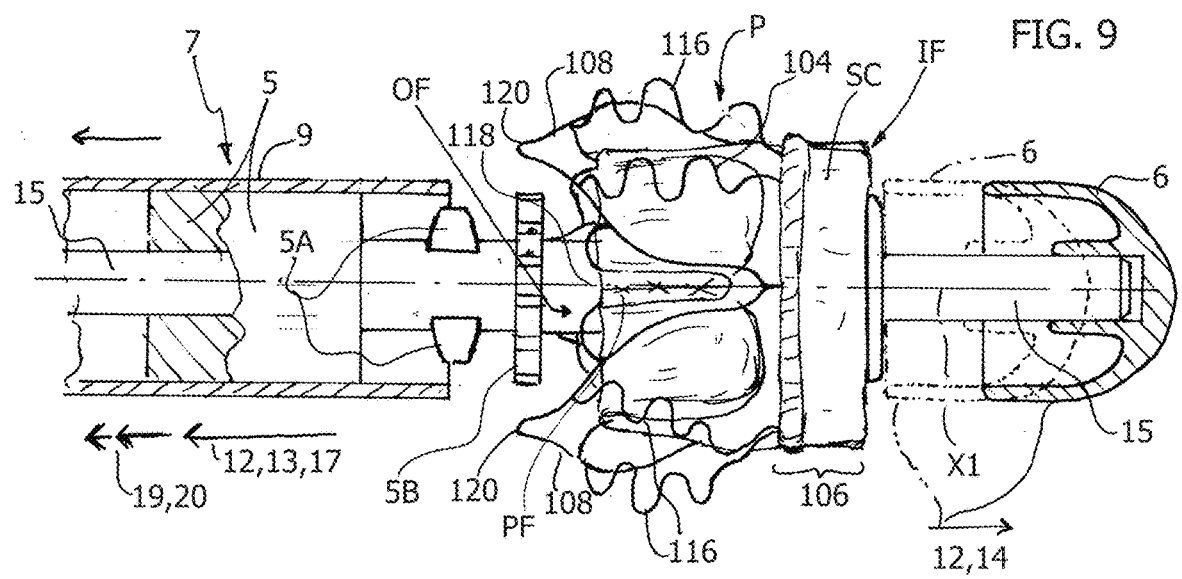

For this purpose, the deployment elements 6, 7 of the carrier portion 4 are operable from a minimum (allowed) mutual distance condition visible in FIG. 3 and associated to a loading/delivery operating condition of the prosthesis, to a larger mutual distance condition visible in FIGS. 4B and 9, and associated to valve deployment/release at the implantation site, and yet to a maximum (allowed) mutual distance condition associated to complete valve deployment/release at the implantation site. The distance referred to is that along the axis X1.

In the minimum mutual distance condition the heart valve prosthesis features a portion, particularly an first end portion (inflow/outflow), of the armature kept radially collapsed between the deployment element 6 and the hub 5, and another portion, particularly again an end portion (outflow/inflow) of the armature kept radially collapsed between the sheath member 9 and the hub 5. The intermediate portions of the valve armature are in various embodiments left free of radial contraction and extend over the interspace between the sheath member 9 and the deployment element 6.

In some embodiments, going through these mutual distance conditions is performed via operation of the drive member (minimum to larger mutual distance), and via operation of the second axially movable element 17 through the shaft member 30 (larger to maximum mutual distance).

As already anticipated, the drive member 11 has drive features 12, 13 which are configured to determine an opposite axial motion of the deployment elements 6, 7. Specifically, by rotating the drive member, e.g. clockwise, the drive features 12, 13 engaging the elements 14, 17 determine an axial motion of the deployment element 6 in a first direction being a distal direction, and an axial motion of the deployment element 7 in a second direction being a proximal direction. By doing so, the deployment element 6 displaces distally of the shaft 2, while the deployment element 7 displaces proximally of the shaft 2, towards the handle 3.

This relative motion allows transitioning from the minimum mutual distance condition to the larger mutual distance condition, thereby allowing the portion of the armature kept radially collapsed by the deployment element 6 to radially expand.

In embodiments the drive features 12, 13 do allow for reverse operation so that a counterclockwise rotation will result in the inversion of first and second directions: the first direction will become a proximal direction, while the second direction will become a distal direction, thereby reducing the mutual distance of the deployment elements along the axis X1. This may be useful primarily to load the valve prosthesis into the carrier portion 4, as well as whenever deployment of the armature portion associated to the deployment element 6 is not completed yet and is deemed unsatisfactory for the progress reached thus far. As far as the proximal axial displacement of the deployment element 7, the same occurs with the element 17 in the fully extended position, in so far as the elastic element S biases the portion 20 in abutment at the end of the slots 25, thereby enabling pulling of the portion 20 in a proximal direction by the portion 19, which instead is directly displaced by the drive feature 13.

The drive feature 12 on its hand axially displaces the element 14, which through the rod/shaft member 15 transfers motion to the deployment element 6.

By proceeding further with clockwise rotation, the larger mutual distance condition may be reached whereat, either the flange 23 comes into contact with the shoulders 37 as visible in FIG. 4A, or the mutual distance achieved is deemed enough by the practitioner to proceed further with a fast release of the prosthesis.

In the first case (end of travel being reached), the portion 19—and the deployment element 7 including the sheath member 9 accordingly—are not allowed to displace any more proximally under the action of the drive member 11. In this condition, however, a certain degree of overlap remains between the sheath member 9 and the hub 5 (see FIG. 4B), so that full release of the prosthesis at the implantation site may not be attained. On the other hand, this condition generally corresponds to a stage of the implantation procedure wherein the prosthesis may be considered already optimally positioned at the implantation site, so that the remainder of the deployment calls for a conclusion as quickly as possible.

In the second case (end of travel not reached, but prosthesis ready for final release), once again a certain degree of overlap remains between the sheath member 9 and the hub 5 (see FIG. 4B), but full release of the prosthesis at the implantation site may be attained anyway by the action of the sole drive member 11. That is, if the practitioner were to change his/her mind and proceed with final release using the sole drive member, that option is still available.

In either case, this is where the arrangement of the axially movable element 17 may come into play.

The portion 20 has an extra share of axial displacement provided by the sliding coupling between the portions 19 and 20. The extra share of axial displacement is a proximal displacement of the portion 20 relative to the portion 19 which results in an equal proximal motion of the sheath member 9 to the condition of maximum mutual distance allowed by the design of the instrument 1, or anyway to a condition of mutual distance determined by the sum of the distance travelled by virtue of the drive member 11, and the extra share of axial displacement allowed by the portion 20 relative to the portion 19.

The additional travel may be covered by gripping the shaft member 18 and pulling the same proximally towards the handle 3. This may be done, for example, by holding the handle 3 in one hand, and pulling the shaft member 18 back (proximally) with the other hand. This will very rapidly retract the sheath member 9 from the hub 5 removing the remaining overlap and fully releasing the valve. The extent of the axial travel that can be covered this way may depend on the length of the slots 25 and/or the solid length of the elastic element S, and/or the axial distance at rest (i.e. in the fully extended condition of the element 17) between the overlapping portions 19 and 20, whatever prevail(s).

The coverage of this extra axial travel by the deployment element 7 occurs independently of the drive member 11, as the same is not configured to control this particular relative sliding of the portions 19 and 20. Note that in the first case the drive member 11 cannot anyway control any further movement of the deployment elements once the condition of FIG. 4A has been reached.

As far as the second case, which may generally be a preferred option, it is worth noting that the extra axial travel from the relative motion between the portions 20 and 19 is available anytime, and not necessarily at the end of the operational range of the drive member 8 (which is instead first case domain). Accordingly, the axial travel of portion 19 through the handle 3 may be preferably sized and dimensioned so as to allow a full deployment of the prosthesis solely by the action of the drive member 11, in order not to call for a mandatory action on the movable element 17 to terminate the release of the prosthesis, while leaving the design of the instrument 1 open to the possibility of a fast (final) release at the discretion of the practitioner. If the practitioner wants so, then resort to the extra travel feature may be made. If the practitioner is more familiar/comfortable with a release provided by manipulation of a single drive member—such as the drive member 11—the option is available to complete the release with the sole action of the drive member.

It follows, more in general, that the first case is actually a sub-species of the second case wherein the extra axial travel of the deployment element 7 independently of the drive member 11 is called into action at the end of the axial travel made available by the design of the drive feature 13 and/or the second portion 19 engaging the drive feature 13.

Figure 6A:
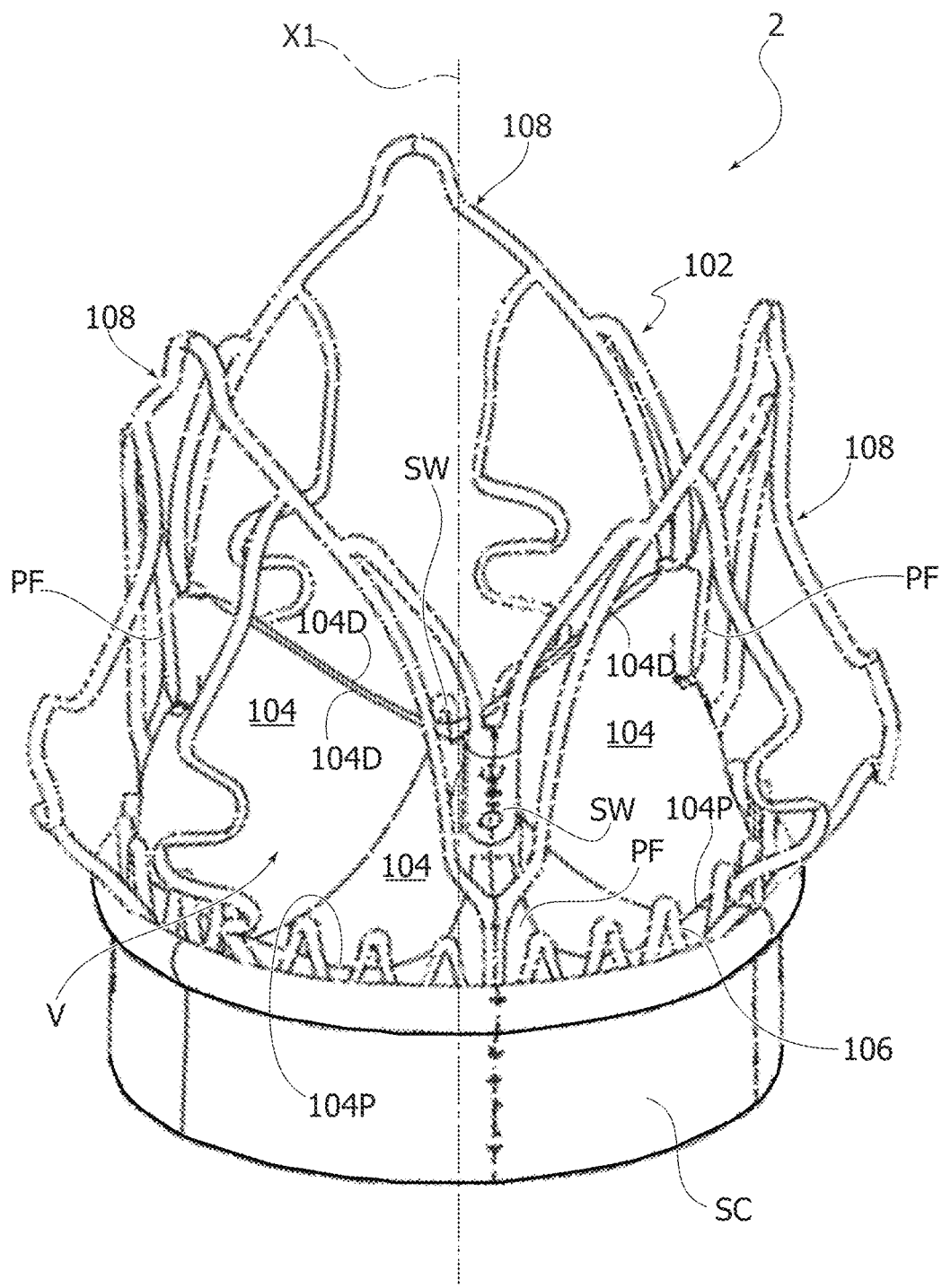
FIGS. 6A and 6B are perspective views of a heart valve prosthesis that may be deployed by the deployment instrument of the embodiments.
Figure 6B:
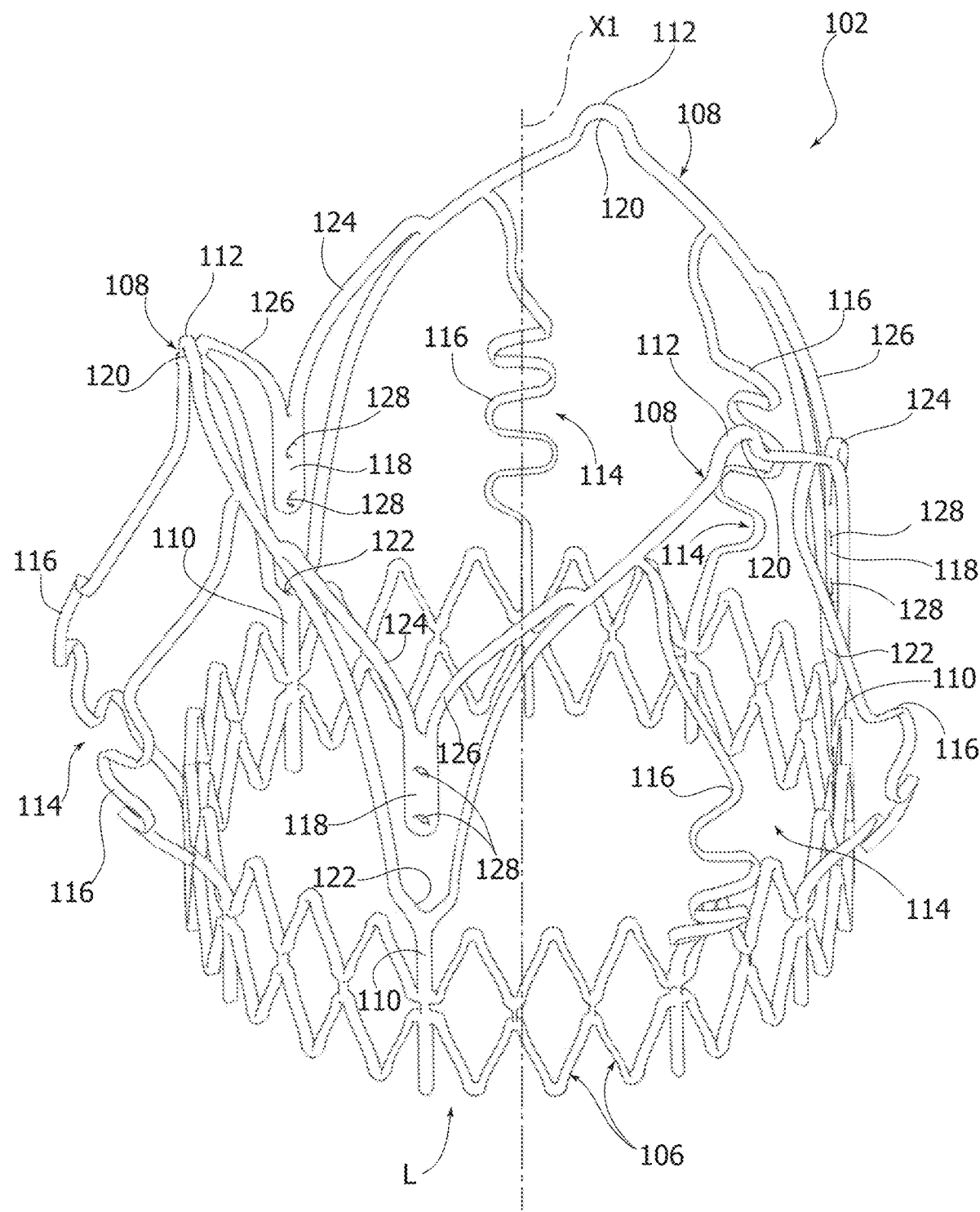
Figure 7:
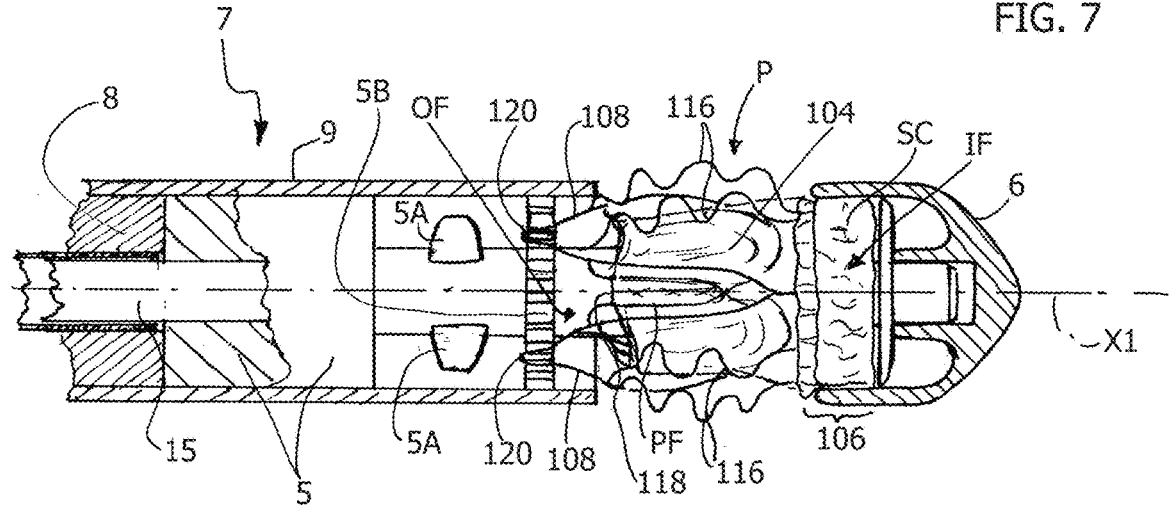
FIGS. 7 to 9 are representative of an exemplary deployment sequence involving the prosthesis of FIGS. 6A and 6B.
Figure 8:
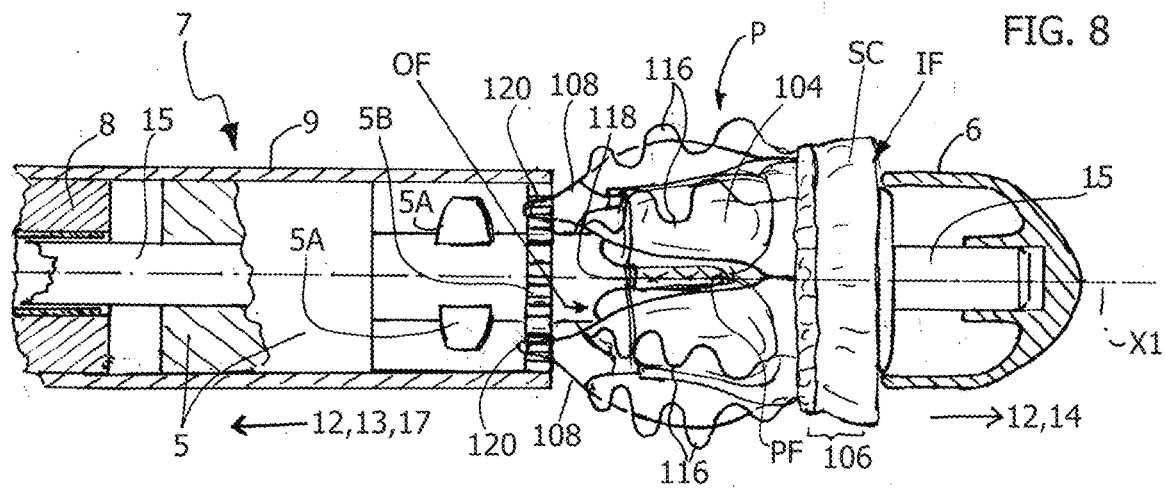

FIGS. 7 to 9 illustrate an exemplary deployment sequence applicable to a heart valve prosthesis P shown in FIGS. 6A, 6B.

With reference to FIGS. 6A and 6B, the heart valve prosthesis P includes an armature 102 for anchorage of the valve prosthesis at an implantation site. The armature 102 defines a lumen for the passage of the blood flow and has a longitudinal axis X2.

The prosthesis P also includes a set of prosthetic valve leaflets 104 supported by the armature 102 and configured to move, under the action of blood flow (which has a main flow direction roughly corresponding to that of the axis X1):

in a radially divaricated condition to enable the flow of blood through the lumen in a first direction, and in a radially contracted condition, in which the valve leaflets 104 co-operate with one another and block the flow of blood through the prosthesis 1 in the direction opposite the first direction. This is commonly referred to as leaflet coaptation.

The prosthetic leaflets 104 may be in any number compatible with operation as replacement heart valve. In one embodiment, the set includes a pair of leaflets. In another embodiment, such as that shown in the figures, the set includes three prosthetic valve leaflets 104 (e.g. for an aortic valve prosthesis). In yet another embodiment, the set may include four leaflets 104.

The armature 102 includes an annular part 106, and a pattern of arched struts 108 carried by the annular part 106. The annular part 106 has a structure which can expand from a radially contracted condition, associated to delivery of the prosthesis to implantation site, to a radially expanded condition wherein the prosthesis is withheld at the implantation site. In these embodiments, the annular part may have a mesh structure including an annular pattern of multiple strut clusters (cells) having polygonal shape (hexagonal, rhomboidal, etc.).

In various embodiments, the annular part is covered by a cuff such as the sealing cuff SC to provide sealing at the implantation site, the cuff being arranged outside of the lumen of the armature 102. Advantageously, the cuff may be sewn or stitched to the annular part 106. The annular part 106 with the sewing cuff attached thereto provides an inflow portion of the heart valve prosthesis P.

As said, depending on the technique used to manufacture the valvular sleeve, wherein the cuff SC may be integral with the set of prosthetic valve leaflets 104.

The pattern of arched struts 108 includes proximal ends 110 connected to the annular part 106, and distal ends 112 spaced axially from the proximal ends 110 and arranged at an end of the armature 102 opposite the annular part 106. In various embodiments, the distal ends 112 coincide with distal ends of the armature 102, and in embodiments where the distal end of the armature 102 coincides with a distal end of the prosthesis 100 as a whole, the distal ends 112 coincide with a distal end of the prosthesis as well.

The armature 102 further includes:
 a plurality of sets 114 of anchoring formations 116 configured to protrude radially outwardly of the annular part 106, each set 114 being supported by at least one of the annular part 106 and a corresponding arched strut 108, and
 a plurality of support posts 118, each supported by adjacent arched struts 108, wherein the sets 114 of anchoring formations 116 alternate with the support posts 118 around the longitudinal axis X1. In various embodiments the support posts 118 are cantilevered to adjacent arched struts 108 and are configured as fixing locations for the prosthetic valve, specifically for the pleat formations PF at the commissural points of the valve.

Each arched strut 108 extends from a first proximal end 110, to a distal end 112, then to a second proximal end 110 in a valley-peak-valley sequence, wherein valleys are located at the proximal ends 110, and peaks are located at the distal ends 112. In various embodiments the pattern of arched struts includes three adjacent and preferably identical arched struts 108 (such as in the figures).

The pattern of arched struts 108 includes distal portions 120 located at the distal ends 112, and inter-strut portions 122 located at the proximal ends 110. The distal portions 120 may be shaped so as to provide a marked local variation in the shape of the strut, for example by exhibiting a C-shape as shown in the figure. The distal portions 120 may provide coupling locations for other devices such as a valve holder or a hub of a carrier portion of a delivery catheter. In other embodiments, the distal portions 120 may be provided as closed-loop structures such as eyes or eyelets. The pattern of arched struts 108, and particularly the distal ends with the distal portion 120 thereof provide an outflow portion of the prosthesis P.

In various embodiments, the inter-strut portions 122 are essentially V-shaped and are defined by the roots of the adjacent arched struts departing from the same proximal end 110. In certain embodiments, the inter strut portions 122 may exhibit a Y-shape such as, for instance, that shown in the figure wherein each inter-strut portion 122 extends through the mesh of the annular part 106. Alternatively, they may exhibit a U-shape. In these embodiments, the mesh of the annular part 106 is provided as a sequence of rhomboidal strut clusters (cells) sequentially connected to each other at endpoints of a diagonal line (typically the shortest diagonal) and exhibiting accordingly an identical circular pattern of free ends on opposite sides of a circumference extending through the sequence of the connection points. The Y-shaped inter-strut portion 122 is thus integrally formed at a selected connection point between two adjacent rhomboidal strut clusters, and typically extends no further than the proximal end of the armature 102.

The support posts 118 are angularly arranged at an inter-strut location, i.e. a circumferential location arranged at an area where an inter-strut portion 122 (as well as—accordingly—a proximal end 110 shared by two adjacent arched struts 108) is provided. The support posts may be advantageously provided as cantilevered to both the adjacent arched struts 8 intervening at an inter-strut portion 122 via a first and a second cantilever struts 124, 126, each connected to a corresponding one of said adjacent arched struts 8 as shown in the figures. The cantilever struts 124, 126 merge into each corresponding post 118 starting from locations on respective arched strut 108 approximately halfway through the portion of the arched strut 108 extending from a proximal end 110 to a distal end 112. The connection points at which the Y-shaped inter-strut portion 122 is formed may be chosen so that the same portions are evenly spaced (angular-wise) around the axis X1. The same applies to the support posts 118, which may be arranged so as to be evenly spaced (angular-wise) around the axis X1.

In the embodiment shown in the figure, the armature 102 comprises three arched struts 108, three posts 118 spaced 120° around the axis X1, and three sets 114, so that the sequence around the axis X1 is post 118—set 114—post 118—set 114—post 118—set 114 (in this sense, even the struts 108 and the sets 114 do follow a 120 degree-like distribution). In this embodiment the three sets 114 include each a pair of anchoring formations 116, wherein each set 114 (and accordingly each anchoring formation 116) extends bridge-wise between the annular part 106 and the corresponding arched strut 108.

With reference to FIG. 7, the prosthesis P is loaded into the deployment instrument 1 so that the annular part 106 (and the sealing cuff thereon) is held in a radially contracted condition by the first deployment element 6, while the distal portions 120 at distal ends of the arched struts 108 are held in a radially contracted condition by the second deployment element 7 (sheath 9 thereof). The sheath 9 may be guided during deployment by spoke members 5A protruding radially from the hub 5, wherein the spoke members 5A provide radial support to the sheath 9. Furthermore, in embodiments, the distal portions 120 engage to a toothed ring member 5B that likewise protrudes radially from the hub 5. Engagement of the toothed ring member 5B may occur so that the distal portions 120 sit astride of a respective tooth of the toothed ring 5B as visible in FIGS. 7 to 9, wherein each respective tooth on its hand protrudes into the distal portion 120. This prevents i.a. unwanted axial displacement of the prosthesis, as well as unwanted rotation of the prosthesis around the axis X1 during deployment.

The spoke members 5A and the toothed ring member 5B may be provided integral with the hub 5 (one toothed ring 5B and three spokes 5A 120 degrees apart).

The anchoring formations 116 are left radially unconstrained as in embodiments there is no deployment element that extends axially over the anchoring formations 116 to radially constrain the same. Accordingly, all of the elements located in the same axial region as the anchoring formations 116 are arranged with no radial constraint (this includes, i.a., the posts 118 as well as the pleat formations PF).

With reference to FIG. 8, operation of the drive member 12 results in an increase in mutual distance between the deployment elements 6 and 7, with release of an inflow portion IF of the prosthesis P corresponding to the portion previously held radially collapsed by the deployment element 6. The motion directions of each of the deployment elements 6, 7 are associated to a composite reference number which bears in sequence the elements involved in the driving action. As may be noticed, the motion of deployment element 7 is controlled by driving member 12, second driving feature 13, and second axially movable element 17 (portions 19 and 20 moving as one). The motion of deployment element 6 is controlled, on its hand, by driving member 12 and first axially movable element 14. As may be seen in the figure, in embodiments an outflow portion OF of the prosthesis P is still substantially held radially contracted by the sheath 9, wherein the outflow portion OF includes i.a. the distal portions 120 of the arched struts 108.

Then, FIG. 9, full deployment of the prosthesis P is shown, wherein both the sheath 9 and the deployment element 6 are clear of the prosthesis P.

This eventually releases the outflow portion OF and achieves full deployment of the prosthesis P. The exemplary condition shown in FIG. 9 may be reached, as per the above, either:
- by operating the driving member 12 to cover all of the available travel(s) for the deployment elements 6, 7, which is represented by the upper left composite reference in FIG. 9 once again involving elements 12, 13, 17 for the deployment element 7, combined with composite reference on the lower right corner involving elements 12, 14 for the deployment element 6. This corresponds to the condition depicted in solid lines in FIG. 9; or
- by operating the driving member 12 to cover a desired share of the axial travel available for the deployment element 7 (the deployment element 6 at that point will have already released the inflow portion IF), then covering the extra axial travel by means of backward (proximal) displacement of the portion 20 relative to the portion 19, as represented by the composite reference in the lower left corner involving elements 12, 13, 17 (slow proximal/backwards motion) and elements 19, 20 (fast proximal/backwards motion). In this latter case, the position of the deployment member 6 is shown in phantom line (while the ending position of the sheath 9 is the same as above), as the same does not cover all of the available axial travel. The person skilled in the art will thus appreciate that in embodiments disclosed herein the deployment instrument 1 allows for a variable control pattern matching the needs of specific stages of the valve deployment procedure. Through all of the stages wherein the deployment elements 6 and 7 are required to displace at a relatively slow rate, the drive member 8 and the drive features 12, 13 provide the desired displacement rate. Note that the displacement rate may in principle be either equal or different between the two drive features. For example, in some embodiments both drive features may provide for an equal axial displacement—subject to the opposite directions condition above—of the deployment elements 6, 7, while in other embodiments either may have a faster or slower rate than the other. For example, when the drive features 12, 13 are provided as threaded portions such as in embodiments depicted by the figures, this may be achieved by differentiating the thread pitch from one drive feature to the other (given that equal pitches return equal axial displacements). When the drive features 12, 13 are provided as cam tracks, this may be done by varying the cam slope (or other equivalent parameter) between the two drive features. Note also that in some embodiments the drive features 12, 13 may even have an intra-feature variable rate, e.g. by including variable pitch threads over the axial length of the feature (the threads on the axially movable elements 14, 17 will have to be modified accordingly to accommodate multi-pitch operation. If the drive features 12, 13 are provided as cam tracks, these features inherently support variable axial rates, so the modification can be done easily.

When—instead—a fast displacement is required to quickly bring the valve release to an end, the features of the axially movable member 17 come into play allowing for an extra travel that can be controlled independently of the drive member 11, and ultimately in a different way, particularly one that supports such a fast motion.

Naturally, while the ideas and principles of the disclosure remain the same, the details of construction and the embodiments may widely vary with respect to what has been described and illustrated purely by way of example, without departing from the scope of the present disclosure.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

The invention claimed is:

1. A deployment instrument for expandable heart valve prostheses including:
   a shaft having a longitudinal axis;
   a handle at a first end of the shaft; and
   a carrier portion at a second end of the shaft, the carrier portion configured for holding an expandable heart valve prosthesis in a radially collapsed condition for delivery to the implantation site,
   wherein:
   the carrier portion includes a hub fixed to the handle via the shaft, a first deployment element and a second deployment element, each of said first deployment element and second deployment element configured to hold a corresponding portion of an expandable heart valve prosthesis in a radially collapsed condition,
   the handle comprises a drive member including a first drive feature and a second drive feature,
   the first deployment element of the carrier portion is connected to a first axially movable element, the first axially movable element engaging said first drive feature of the drive member, the second deployment element of the carrier portion is connected to a second axially movable element, the second axially movable element engaging said second drive feature of the drive member, wherein operation of the drive member is configured to simultaneously actuate both the first drive feature to axially displace the first deployment element in a first direction and the second drive feature to axially displace the second deployment element in a second direction, said first direction and said second direction being opposite to one another, and further wherein the second axially movable element includes a first portion and a second portion, the first portion engaging the second drive feature, and the second portion being axially movable relative to the first portion to provide an axial displacement of the second deployment element in the second direction independently of the drive member.

2. The deployment instrument of claim 1, wherein the first end of the shaft is a proximal end, and the second end of the shaft is a distal end.

3. The deployment instrument of claim 1, wherein the first direction is a distal direction, and the second direction is a proximal direction.

4. The deployment instrument of claim 1, wherein said first drive feature comprises a first threaded portion and said second drive feature comprises a second threaded portion.

5. The deployment instrument of claim 4, wherein said drive member is a rotary drive member comprising a knob and a stem, the first drive feature being provided on a first surface of the stem, and the second drive feature being provided on a second surface of the stem.

6. The deployment instrument of claim 1, wherein the first portion and the second portion of the second axially movable element are partly overlapping and slidably coupled to one another.

7. The deployment instrument of claim 6, the second axially movable element including an elastic element biasing the second portion away from the first portion.

8. The deployment instrument of claim 1, wherein the shaft has a layered structure.

9. The deployment instrument of claim 8, wherein the shaft includes:
   a first shaft member as middle layer;
   a second shaft member as outer layer; and
   a rod or shaft member as a core,
   wherein:
      the first shaft member connects the hub of the carrier portion to the handle,
      the second shaft member connects the second deployment element to the second axially movable element,
      the rod or shaft member connects the first deployment element to the first axially movable element.

10. The deployment instrument of claim 9, wherein the second shaft member is engaged by diametrically opposite axial extensions protruding from an annular member of the second axially movable element.

11. A deployment instrument for expandable heart valve prostheses, including:
   a shaft having a longitudinal axis;
   a handle at a first end of the shaft; and
   a carrier portion at a second end of the shaft, the carrier portion configured for holding an expandable heart valve prosthesis in a radially collapsed condition for delivery to the implantation site,
   wherein:
      the carrier portion includes a hub fixed to the handle via the shaft, a first deployment element and a second deployment element, each of said first deployment element and second deployment element configured to hold a corresponding portion of an expandable heart valve prosthesis in a radially collapsed condition,
      the handle comprises a drive member including a first drive feature and a second drive feature,
      the first deployment element of the carrier portion is connected to a first axially movable element, the first axially movable element engaging said first drive feature of the drive member,
      the second deployment element of the carrier portion is connected to a second axially movable element, the second axially movable element engaging said second drive feature of the drive member, wherein upon operation of the drive member the first drive feature is configured to axially displace the first deployment element in a first direction, and the second drive feature is configured to axially displace the second deployment element in a second direction, said first direction and said second direction being opposite to one another, and
   further wherein the second axially movable element includes a first portion and a second portion, the first portion engaging the second drive feature, and the second portion being axially movable relative to the first portion to provide an axial displacement of the second deployment element in the second direction independently of the drive member;
   wherein said first drive feature comprises a first threaded portion and said second drive feature comprises a second threaded portion;
   wherein said drive member is a rotary drive member comprising a knob and a stem, the first drive feature being provided on a first surface of the stem, and the second drive feature being provided on a second surface of the stem; and
   wherein said stem is a hollow member, said first drive feature being provided on an inner surface of the stem, and said second drive feature being provided on an outer surface of the stem.

12. A deployment instrument for expandable heart valve prostheses, including:
   a shaft having a longitudinal axis;
   a handle at a first end of the shaft; and
   a carrier portion at a second end of the shaft, the carrier portion configured for holding an expandable heart valve prosthesis in a radially collapsed condition for delivery to the implantation site,
   wherein:
      the carrier portion includes a hub fixed to the handle via the shaft, a first deployment element and a second deployment element, each of said first deployment element and second deployment element configured to hold a corresponding portion of an expandable heart valve prosthesis in a radially collapsed condition,
      the handle comprises a drive member including a first drive feature and a second drive feature,
      the first deployment element of the carrier portion is connected to a first axially movable element, the first axially movable element engaging said first drive feature of the drive member,
      the second deployment element of the carrier portion is connected to a second axially movable element, the second axially movable element engaging said second drive feature of the drive member, wherein upon operation of the drive member the first drive feature is configured to axially displace the first deployment element in a first direction, and the second drive feature is configured to axially displace the second deployment element in a second direction, said first direction and said second direction being opposite to one another, and further wherein the second axially movable element includes a first portion and a second portion, the first portion engaging the second drive feature, and the second portion being axially movable relative to the first portion to provide an axial displacement of the second deployment element in the second direction independently of the drive member;

wherein the first portion includes:
an annular portion wherefrom a first pair of diametrically opposite axial extensions protrude; and
an internal thread provided on the cylindrical inner surfaces of the axial extensions of the first pair and the annular member, the internal thread being configured to engage the second drive feature,
wherein the axial extensions merge at a flange wherefrom a second pair of diametrically opposite axial extensions departs axially away from the first pair of axial extensions.

13. The deployment instrument of claim 12, wherein the axial extensions of the second pair are arranged at a location at right angle relative to the axial extensions of the first pair.

14. The deployment instrument of claim 12, wherein each axial extension of the second pair includes a through axial slot, the axial extensions of the second pair being separated by a pair of axial grooves.

15. The deployment instrument of claim 12, wherein the second portion of the second axially movable element includes an annular member wherefrom a third pair of diametrically opposite axial extensions protrude.

16. The deployment instrument of claim 15,
wherein the axial extensions of the third pair have the same position as the axial extensions in the second pair, and are each provided with a radially protruding plug,
wherein a pair of radially protruding teeth, diametrically opposite, extend from an inner surface of the annular portion and inwardly of the same, while a pair diametrically opposite guide fingers extend axially at said annular portion at positions at right angles relative to those of the radially protruding teeth, and
wherein the guide fingers are aligned with a corresponding through axial slot and slidably engage the same, while the teeth are aligned with the grooves separating the axial extensions of the second pair and are slidable therethrough.

17. A deployment instrument for expandable heart valve prostheses including:
a shaft having a longitudinal axis;
a handle at a first end of the shaft; and
a carrier portion at a second end of the shaft, the carrier portion configured for holding an expandable heart valve prosthesis in a radially collapsed condition for delivery to the implantation site,
wherein:
the carrier portion includes a hub coupled to the handle via the shaft, a first deployment element and a second deployment element, each of said first deployment element and second deployment element configured to hold a corresponding portion of an expandable heart valve prosthesis in a radially collapsed condition,
the handle comprises a drive member that simultaneously causes a first drive feature to axially displace the first deployment element in a first direction and a second drive feature to axially displace the second deployment element in a second, opposite, direction.

18. The deployment instrument of claim 17, wherein the second deployment element is coupled to the second drive feature by a second axially movable member that includes a first portion and a second portion, the first portion engaging the second drive feature, and the second portion being independently axially movable relative to the first portion.

19. The deployment instrument of claim 17, wherein the first drive feature comprises a first threaded portion having first winding threads and the second drive feature comprises a second threaded portion having second winding threads, opposite the first winding threads.

* * * * *